(12) United States Patent
Gon

(10) Patent No.: US 11,125,735 B2
(45) Date of Patent: Sep. 21, 2021

(54) DYNAMIC WAX DEPOSITION TESTING SYSTEMS AND METHODS

(71) Applicant: ChampionX USA Inc., Sugar Land, TX (US)

(72) Inventor: Saugata Gon, Sugar Land, TX (US)

(73) Assignee: ChampionX USA Inc., Sugar Land, TX (US)

( * ) Notice: Subject to any disclaimer, the term of this patent is extended or adjusted under 35 U.S.C. 154(b) by 179 days.

(21) Appl. No.: 15/942,165

(22) Filed: Mar. 30, 2018

(65) Prior Publication Data

US 2018/0284097 A1    Oct. 4, 2018

Related U.S. Application Data

(60) Provisional application No. 62/479,063, filed on Mar. 30, 2017.

(51) Int. Cl.
| | | |
|---|---|---|
| *G01N 33/28* | (2006.01) | |
| *G01N 25/02* | (2006.01) | |
| *B01L 7/02* | (2006.01) | |
| *B01F 11/00* | (2006.01) | |

(52) U.S. Cl.
CPC ...... *G01N 33/2835* (2013.01); *B01F 11/0005* (2013.01); *B01L 7/02* (2013.01); *G01N 25/02* (2013.01)

(58) Field of Classification Search
CPC . B01F 11/0005; C09K 8/524; G01N 33/2835; G01N 33/28; G01N 25/02; G01N 25/12; E21B 37/06
USPC ................. 73/61.62; 507/90, 931; 166/304
See application file for complete search history.

(56) References Cited

U.S. PATENT DOCUMENTS

| | | | |
|---|---|---|---|
| 3,879,177 A | 4/1975 | Andress, Jr. | |
| 4,693,312 A | 9/1987 | Lenderman | |
| 4,997,580 A | 3/1991 | Karydas et al. | |
| 5,918,979 A | 7/1999 | Martin et al. | |
| 6,035,706 A * | 3/2000 | Campagnolo ...... | G01N 33/2811 374/23 |
| 6,558,632 B1 | 5/2003 | Guller et al. | |

(Continued)

FOREIGN PATENT DOCUMENTS

| | | |
|---|---|---|
| CN | 200944096 Y  * | 9/2007 |
| CN | 101576550 A  * | 11/2009 |

(Continued)

OTHER PUBLICATIONS

Wang et al, Evaluation of Effects of Selected Wax Inhibitors on Wax Appearance and Disappearance Temperatures, Petroleum Science and Technology • Jan. 2003 (Year: 2003).*

(Continued)

*Primary Examiner* — David L Singer
(74) *Attorney, Agent, or Firm* — Stinson LLP

(57) ABSTRACT

A system for evaluating wax deposition includes a temperature controlled environment, a container for holding a fluid, the container being positioned in the temperature controlled environment, a cold body extending into the container, a cooling system connected to the cold body and configured to circulate a coolant through the cold body to cool the cold body, and an agitation system configured to produce relative movement between the cold body and the fluid in the container by moving the container and cold body.

20 Claims, 15 Drawing Sheets

(56) References Cited

U.S. PATENT DOCUMENTS

| | | | |
|---|---|---|---|
| 7,417,009 B2 | 8/2008 | Shmakova-Lindeman | |
| 9,163,194 B2 | 10/2015 | Sonne et al. | |
| 2002/0166995 A1* | 11/2002 | Robinson | C10L 1/143 |
| | | | 252/380 |
| 2015/0127315 A1 | 5/2015 | Lavenson et al. | |
| 2016/0115369 A1 | 4/2016 | Soriano, Jr. et al. | |
| 2016/0185917 A1 | 6/2016 | Drummond et al. | |
| 2016/0208601 A1 | 7/2016 | Molla et al. | |
| 2017/0009067 A1 | 1/2017 | Garcia Castro et al. | |

FOREIGN PATENT DOCUMENTS

| | | | | |
|---|---|---|---|---|
| CN | 201885983 U | * | 6/2011 | |
| CN | 103116015 A | * | 5/2013 | |
| CN | 104865149 A | * | 8/2015 | |
| CN | 105203742 A | * | 12/2015 | |
| CN | 105223227 A | * | 1/2016 | |
| CN | 105301039 A | * | 2/2016 | |
| CN | 105334145 A | * | 2/2016 | |
| CN | 105334145 A | | 2/2016 | |
| CN | 205157473 U | * | 4/2016 | |
| CN | 205175878 U | * | 4/2016 | |
| CN | 205175878 U | | 4/2016 | |
| CN | 105699415 A | * | 6/2016 | |
| CN | 105699415 A | | 6/2016 | |
| CN | 205404461 U | * | 7/2016 | |
| CN | 205404461 U | | 7/2016 | |
| CN | 105954471 A | * | 9/2016 | |
| CN | 106442202 A | * | 2/2017 | |
| CN | 106442202 A | | 2/2017 | |
| CN | 106546713 A | * | 3/2017 | |
| CN | 206531850 U | * | 9/2017 | |
| DE | 29706031 U1 | * | 8/1997 | ............... B01L 7/02 |
| WO | 2014/009067 A1 | | 1/2014 | |
| WO | 2016/025749 A1 | | 2/2016 | |

OTHER PUBLICATIONS

Zhu et al, Evaluation of Wax Deposition and Its Control During Production of Alaska North Slope Oils, Oil & Natural Gas Technology DOE Award No. DE-FC26-01NT41248 (Year: 2008).*
Stuart, Linear shaker—SSL2 (Year: 2013).*
Techbox Systems, Dynamic Differential Scale Loop DSL Specialists: Techbox Systems Multi-Place Wax Cold Finger (CF6) (Year: 2015).*
Morozov et al, New Insight into the Wax Precipitation Process: In Situ NMR Imaging Study in a Cold Finger Cell, American Chemical Society, Energy Fuels 2016, 30, 9003-9013 (Year: 2016).*
Vinci Technologies, Multi-Place Cold Finger (MCF series) (Year: 2016).*
Techbox Systems, Multi Place Cold Finger (CF6) (Year: 2020).*
CN101576550A—machine translation (Year: 2020).*
CN206531850U—machine translation (Year: 2020).*
CN103116015A—machine translation (Year: 2020).*
CN104865149A—machine translation (Year: 2020).*
CN105203742A—machine translation (Year: 2020).*
CN105223227A—machine translation (Year: 2020).*
CN105301039A—machine translation (Year: 2020).*
CN105334145A—machine translation (Year: 2020).*
CN105699415A—machine translation (Year: 2020).*
CN105954471A—machine translation (Year: 2020).*
CN106442202A—machine translation (Year: 2020).*
CN106546713A—machine translation (Year: 2020).*
CN200944096Y—machine translation (Year: 2020).*
CN201885983U—machine translation (Year: 2020).*
CN205157473U—machine translation (Year: 2020).*
CN205175878U—machine translation (Year: 2020).*
CN205404461U—machine translation (Year: 2020).*
Paso et al, Bulk Stabilization in Wax Deposition Systems, Energy & Fuels 2004, 18, 1005-1013 (Year: 2004).*
Ridzuan et al, Screening of factor influencing wax deposition using full factorial experimental design, Petroleum Science and Technology, 34:1, 84-90, DOI: 10.1080/10916466.2015.1122625 (Year: 2016).*
Couto, G. H., et al., "An Investigation of Two-Phase Oil/Water Paraffin Deposition," SPE 114735, SPE Production & Operations, Feb. 2008, First presented to Offshore Technology Conference, Houston, Texas, May 1-4, 2006 as paper OTC 17963, pp. 49-55.
Hunt, Jr., E. B., "Petroleum Transactions, Laboratory Study of Paraffin Deposition," Journal of Petroleum Technology, SPE 279, Nov. 1962, pp. 1259-1269.
Kasumu, A. S., et al., "Solids Deposition from Wax-Solvent-Water "Waxy" Mixtures Using a Cold Finger Apparatus," Energy & Fuels, 2015, pp. 501-511, vol. 29.
Leiroz, A. T., et al., "Paraffin Deposition in a Stagnant Fluid Layer Inside a Cavity Subjected to a Temperature Gradient," Proceedings of the 10th Brazilian Congress of Thermal Sciences and Engineering, Paper CIT04-0349, 2004, 10 pages.
Valinejad, R., et al., "An Experimental Design Approach for Investigating the Effects of Operating Factors on the Wax Deposition in Pipelines," Fuel, 2013, pp. 843-850, vol. 106.
Weispfennig, K., et al., "Advancements in Paraffin Testing Methodology," SPE International, SPE 64997, Presentee at the 2001 SPE International Symposium on Oilfield Chemistry in Houston, Texas, on Feb. 13-16, 2001, pp. 1-6.

* cited by examiner

DYNAMIC WAX DEPOSITION TESTING SYSTEMS AND METHODS

CROSS REFERENCE TO RELATED APPLICATIONS

This application claims the benefit of U.S. Provisional Patent Application Ser. No. 62/479,063 filed on Mar. 30, 2017, the disclosure of which is incorporated herein by reference in its entirety.

FIELD OF INVENTION present invention relates generally to systems and methods for evaluating wax deposition from wax-containing fluids, and more particularly to systems and methods for evaluating how different chemicals affect wax deposition from fluids produced from oil fields.

BACKGROUND

Crude oil is a mixture of a large number of different hydrocarbons. The exact composition varies from one region to the next and even from one oil field to the next. The saturated long chain hydrocarbons (typically C16 and higher) are known as paraffin. Depending on the type of crude oil, it can contain a significant amount of paraffin. Paraffin crystals come out of the liquid oil phase below a certain temperature known as "wax appearance temperature" or (WAT). As the fluid produced by an oil field is pumped through a pipeline it can experience cooling due to a temperature gradient between ambient temperature and the production fluid or pressure drop in the line leading to Joule Thomson cooling. Paraffin crystals can deposit on cold surfaces (mostly on the interior pipe surface). Paraffin deposition in oil-field production and flow lines can cause fouling and plugging issues and may cause further damage to the installed equipment. It can lead to production upsets and loss for the customers. Cooling of paraffin-containing oil can further cause gelation of the oil and thus increase its viscosity and reduce the pumping efficiency. Paraffin-related issues can be more severe in deep sea platforms/FPSOs.

Most oil-fields use mechanical or chemical methods to inhibit paraffin deposition. For example, Nalco Champion offers several types of paraffin-combating products to its customers for combating paraffin deposition. Paraffin inhibitors (sometimes referred to as PIs) are typically polymers that have structural similarity with wax. These types of chemicals are believed to modify the wax crystal structure and slow down the agglomeration and deposition mechanism of wax. On the other hand, paraffin dispersants (sometimes referred to as PDs) are generally various types of surfactants that interact with the wax crystals to enhance their dispersion capability in the production fluid. The dispersants can help retain more wax crystals in the bulk fluid and thereby reduce the deposition probability of the wax crystals. There are several different types of chemicals available and performance of the different types of chemicals is known to be sensitive to the particular characteristics of the specific oil produced by the oil field. For example, field experience suggests to some that water cut (i.e. the percentage of water in the fluids produced by the oil field) can affect P I/PD performance. There are competing arguments about water cut sometimes improving or deteriorating performance of different PI/PDs. Other variables, such as temperature and chemical variations also affect the performance of PI/PDs.

Thus, the oil industry has developed a practice of running small-scale laboratory tests to identify suitable PI/PDs for use with specific oil production fluids sampled from the field. The industry currently relies heavily on a test that uses a "Cold Finger" for screening of paraffin inhibitors for dry oil (i.e. oil that contains little or no water). In a conventional cold finger test, crude oil is placed in a glass bottle along with a magnetic stirrer. The bottle is then placed on a magnetic stir plate inside a hot bath, usually at a target temperature that is slightly above or below the wax appearance temperature (WAT) of the oil. The magnetic stir plate generates a rotating magnetic field that causes the magnetic stirrer to rotate at the bottom of the bottle, and thereby agitate the fluid. A metal finger is inserted vertically into the oil from the top of bottle. A chiller cools a coolant that is circulated through the cold finger to maintain a target temperature (as per the test condition) for the finger, which serves as a cold surface for paraffin deposition. The performance of a paraffin inhibitor may be evaluated by seeing how much paraffin deposits on the cold finger.

Although cold fingers can differentiate among paraffin inhibitors, they are known for their limitations in screening paraffin dispersants. For example, although field case studies often find paraffin dispersants to be effective treating agents for preventing paraffin deposition, conventional laboratory cold finger tests often show them to be ineffective at limiting wax deposition. Conventional cold finger tests can also be unreliable when the fluid includes brine, which is commonly the case for fluids produced by oil fields.

The present inventor has developed improved systems and methods, which will be described below, for testing wax deposition under varying conditions and in the presence of different chemicals.

BRIEF DESCRIPTION OF THE DRAWINGS

Corresponding reference characters indicate corresponding parts throughout the drawings.

DETAILED DESCRIPTION

Figure 1:
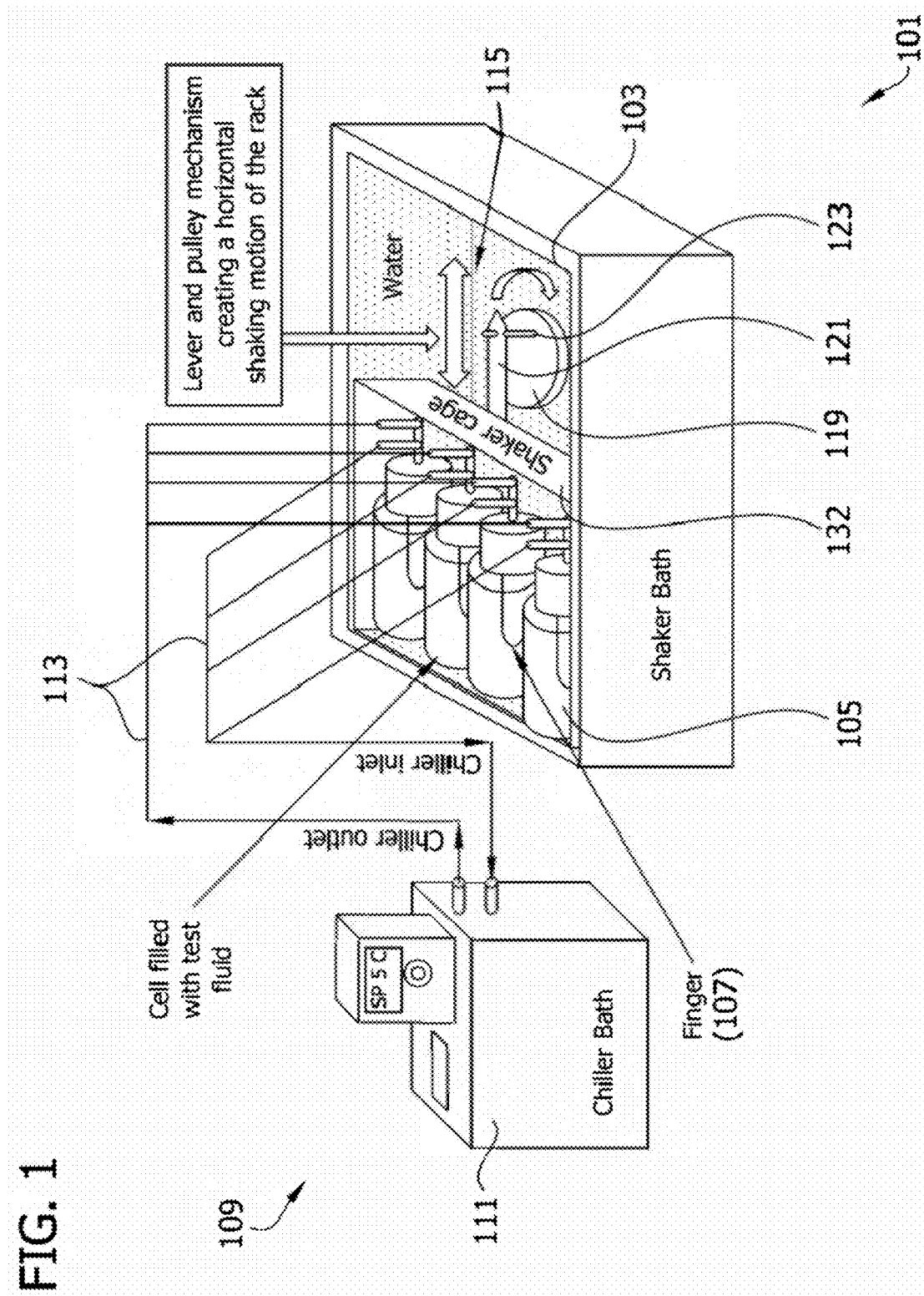
FIG. 1 is a schematic diagram of one embodiment of a wax deposition test system.

Referring to FIGS. 1-4, one embodiment of a system for evaluating wax deposition is generally designated 101. The system 101 includes a temperature controlled environment 103 (e.g., a temperature controlled bath) and one or more containers 105 positioned in the temperature controlled environment. Although the system 101 illustrated in the drawings uses a temperature controlled bath 103, it is understood the temperature controlled environment could be an oven or other environment that can be maintained at a desired temperature. For example, a heating coil, heat tape, or other heater(s) could be wrapped around or placed adjacent the containers.

In the embodiment illustrated in FIG. 1, there are four containers 105. However, the number of containers can vary. The containers 105 are suitably relatively small in volume. For example, the containers 105 are suitably configured to contain no more than about 1 liter (e.g., from about 20 ml to about 1 liter) of test fluid. A cold body 107 extends into each container 105. In general, the cold body can have any size and shape as long as it can be extended into a container containing a fluid to be tested. For example, in the illustrated embodiment, the cold body 107 is in the shape of a cold finger. However, it is noted that the cold finger 107 illustrated in the drawings could be replaced with different cold finger, a disk-shaped cold body, or a cold body having other geometric shapes if desired.

When the cold body 107 is a cold finger, the length of each cold finger 107 can vary depending on the size of the container 105. The cold fingers 107 are suitably long enough to extend from the open end of the container at least half of the distance to the opposite end of the container. For example, the cold finger 107 suitable has a length in the range of about 0.5 inches to about 8 inches. The cold fingers 107 are suitably each mounted on a disk (e.g., a non-metallic disk) that has an outside diameter similar to the size of the opening at the end of the respective container 105, which functions to hold the cold finger in a central position in the opening and on a central axis of the container. A cap 110 (e.g., a threaded cap) on the end of the container 105 holds the cold finger 107 and the disk in position in the opening of the container and seals the container. Although the cold fingers 107 in the illustrated embodiment are substantially aligned with the longitudinal axis of the containers 105, the containers may have a different orientation from the containers if desired. Broadly speaking, the longitudinal axis of one all of the cold fingers 107 can be at any angle (0-180 degrees) relative to the longitudinal axis of the respective container 105. It is also possible that the containers may not have any longitudinal axis. Also, regardless of the shape of the container one or more of the cold fingers could be configured as a cold body that does not have any longitudinal axis if desired.

Each cold body 107 (e.g., cold finger) is connected to a cooling system 109 configured to circulate coolant through the cold body to cool the cold body. As illustrated in FIG. 1, for instance, the cooling system 109 suitably includes a chiller 111 that cools a bath of water or other coolant (e.g., a mixture of ethylene glycol and water) and fluid lines 113 that circulate the coolant through the cold fingers 107.

The system 101 also includes an agitation system 115 configured to move the containers 105 and cold bodies 107 in a manner that includes a horizontal component. The agitation system 115 is suitably configured to move the container 105 and cold bodies 107 in a manner that creates ongoing relative movement between the cold body and the fluid in the container due to the momentum of the fluid and the movements (e.g., bi-directional movements) of the container and cold body. In the illustrated embodiment, for example, the agitation system 115 is a shaker system configured to move the containers 105 and the cold fingers 107 therein back and forth in a reciprocating motion. The motion is suitably a substantially linear reciprocating motion, as in the illustrated embodiment, although this is not required. The agitation system could be configured to move the containers and cold bodies in an orbital or circular motion within the broad scope of the invention.

Figure 5:
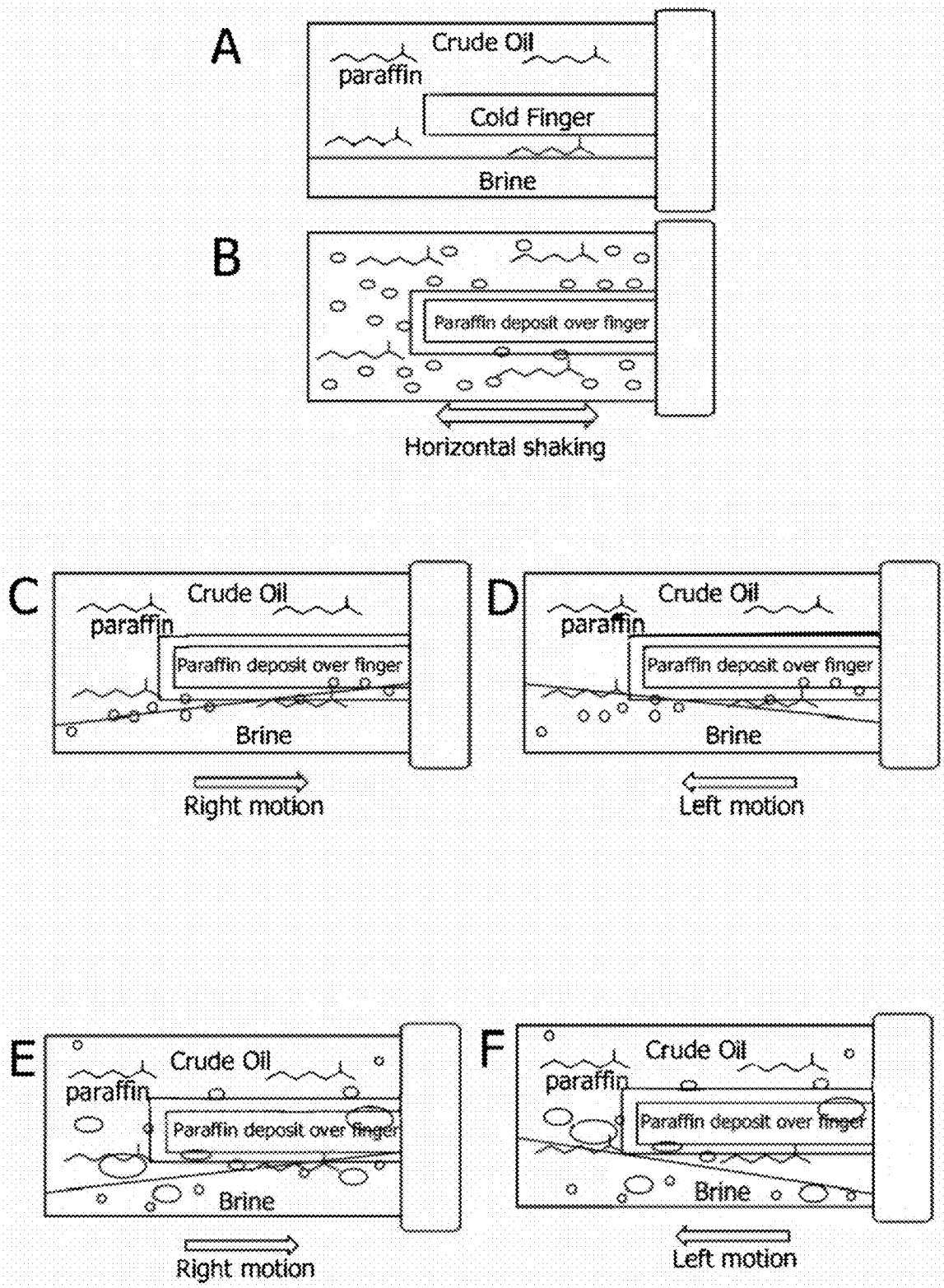
FIG. 5 is schematic diagram illustrating various possibilities (panels A-D) for mixing of oil and water inside a container of the wax deposition test system before and during shaking.

As illustrated in FIGS. 1 and 5 the cold finger 107 for each container 105 has a longitudinal axis and is oriented so the longitudinal axis of the cold finger extends in a horizontal direction. For example, the longitudinal axis of the cold finger 107 is suitably substantially horizontal. However, it is possible that longitudinal axis of one or all of the cold fingers 107 may extend in a direction that includes a vertical component in addition to a horizontal component. The shaker system 115 is configured to move the containers 105 back and forth in a direction that include a component that is parallel to the longitudinal axes of the cold fingers 107. In the illustrated embodiment, the longitudinal axes the cold fingers 107 are substantially parallel to one another and the shaker system 115 is configured to move the containers 105 and the cold fingers 107 therein back and forth in a direction that includes a component that is substantially parallel to the longitudinal axes of the cold fingers. However, it is understood there could be some deviation in the orientations of the cold fingers 107 relative to one another without departing from the scope of the invention. It is also understood there could be some deviation in the orientation of the cold fingers 107 and the direction of movement of the containers 105 by the shaker system 115.

Figure 2:
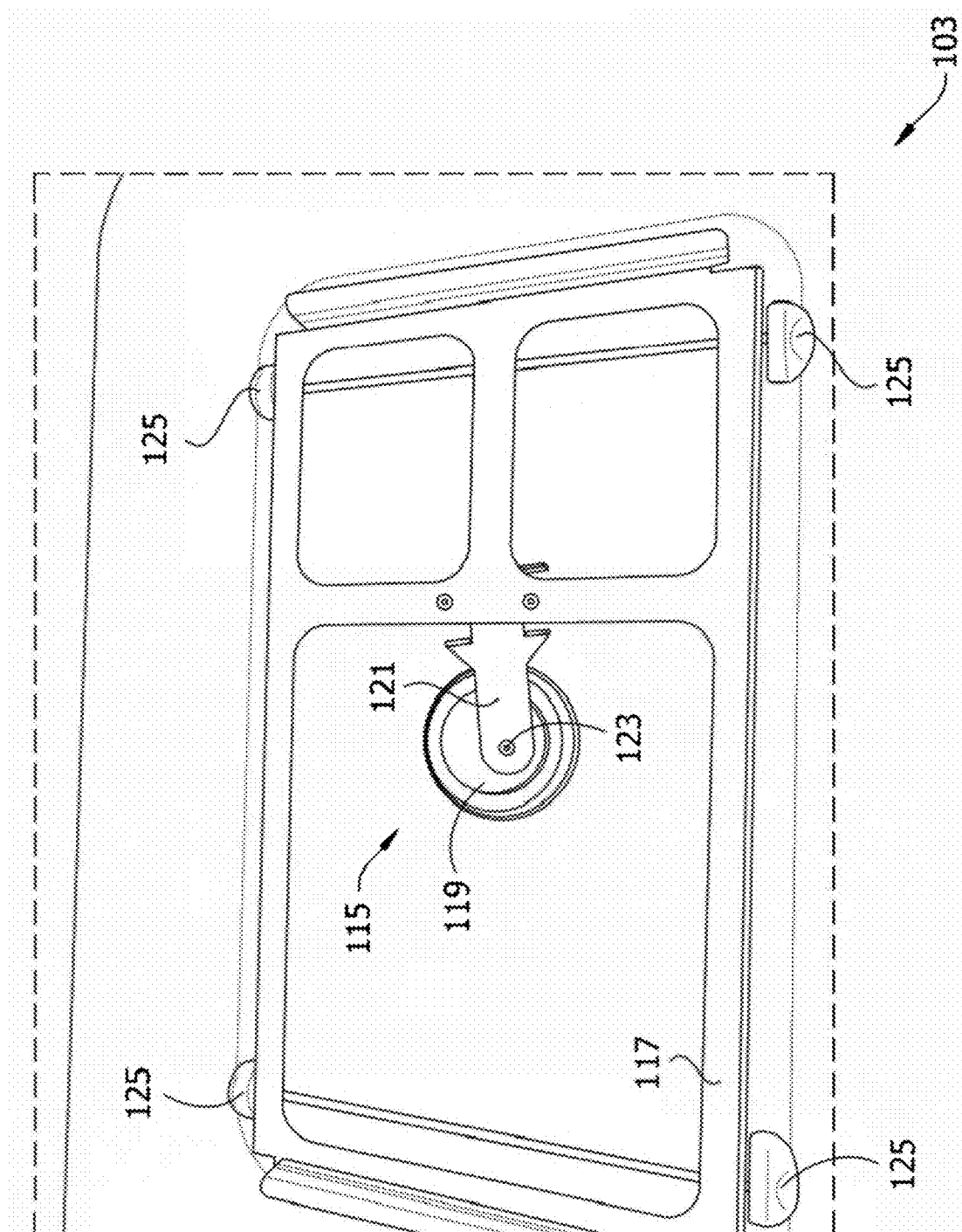
FIG. 2 is a photograph showing parts of one embodiment of a shaker system of the wax deposition test system in FIG. 1.

FIG. 2 shows one embodiment of a suitable shaker system 115 for use with the system 101 in more detail. The shaker system 115 includes a carriage 117 for supporting the containers, a motor-driven crank 119, and a connecting rod 121 connecting the crank to the carriage so rotation of the crank by a motor (not shown) drives movement of the carriage. The crank 119 is suitably in the form of a crank wheel mounted in the bottom of the temperature controlled bath 103. The crank could be a crank arm instead of a wheel if desired. The connecting rod 121 is suitably pivotally connected to the crank 119 and also pivotally connected to the carriage 117. For example, the connecting rod 121 is suitably connected to the crank 119 by a pin 123 secured to the crank at a position offset from the center of the crank. A similar pin (not shown) is suitably secured to the carriage 117 (e.g., the underside of the carriage) to provide a connection point between the carriage and the end of the connecting rod opposite the crank 119. The carriage 117 is suitably mounted on wheels 125 that are positioned to roll back and forth on the bottom of the bath 103.

In this particular shaker system 115, the carriage 117 moves back and forth in a linear reciprocating harmonic oscillatory motion. The length of each stroke is suitably in the range of about 5 mm to about 100 mm (e.g., about 10 mm to about 30 mm). The speed of the motor is suitably selectively adjustable to allow adjustments to the number of strokes per minute. For example, the stroke rate is suitably adjustable from about 20 strokes per minute to about 200 strokes per minute. It is understood a scotch yoke or other mechanism could be used instead the mechanism illustrated in FIG. 2 to produce a linear reciprocating harmonic oscillatory motion if desired. It is also understood that the motion does not need to be pure linear reciprocating motion and that other motions, such as circular or oblong orbital motions, could also be used instead without departing from the broad scope of the invention.

Figure 3:
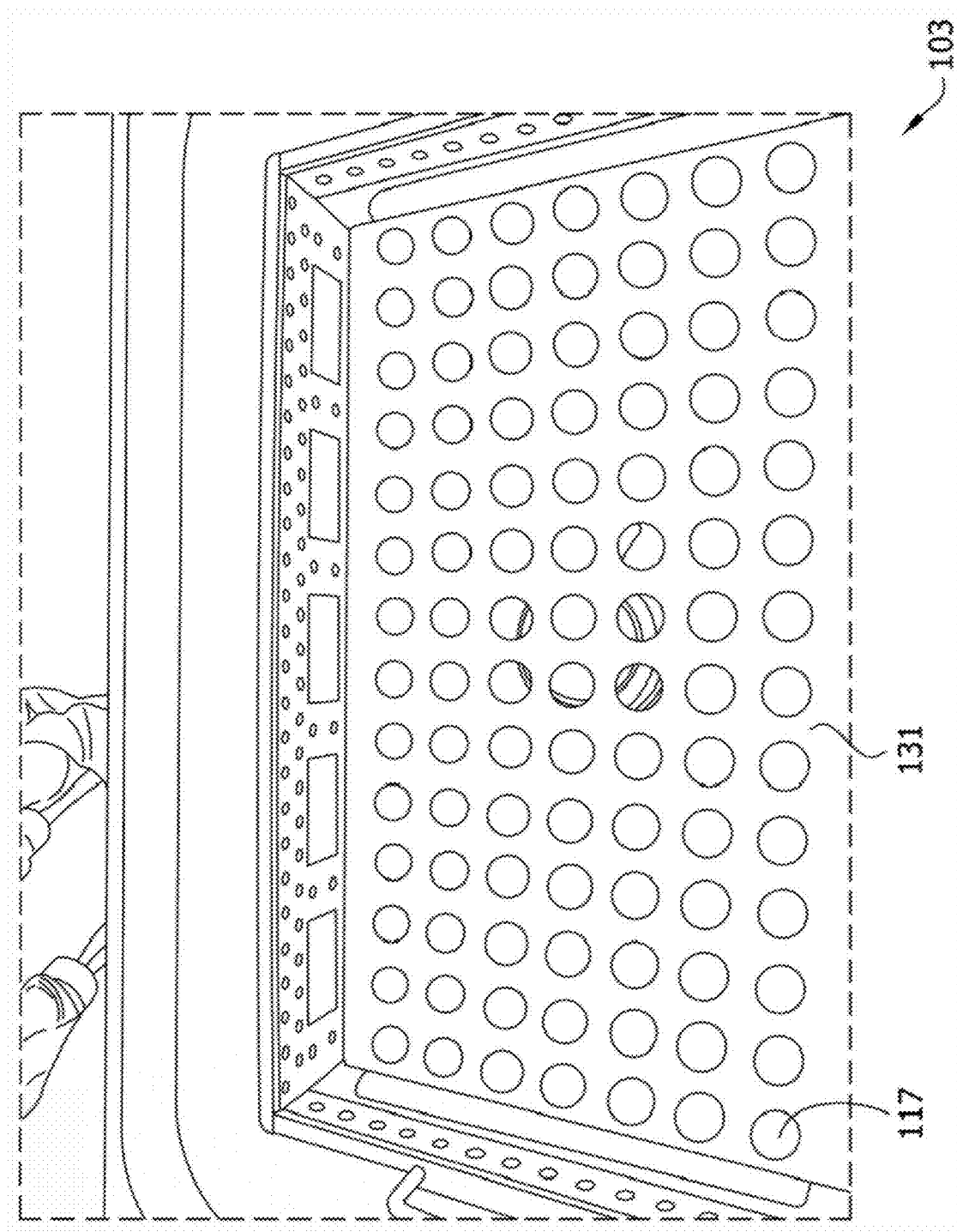
FIG. 3 is a photograph similar to FIG. 2 showing additional parts of the shaker system.
Figure 4:
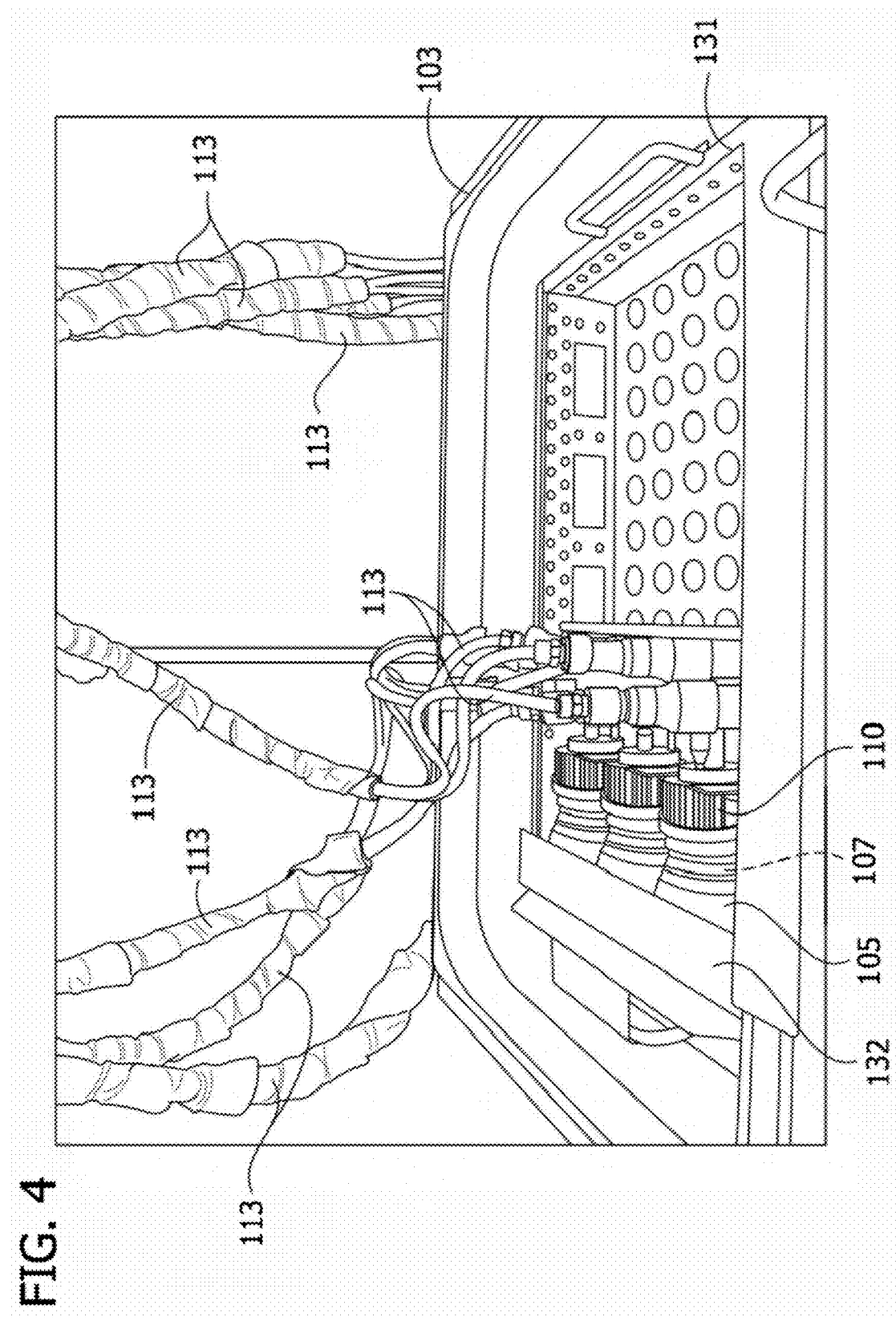
FIG. 4 is a photograph of a portion of the wax deposition test system illustrated in FIG. 1.

Referring to FIGS. 3 and 4, the system 101 suitably includes a tray 131 (broadly, a "support") that is mounted on the carriage 117 for movement with the carriage. The containers 105 are loaded onto a custom built shaker cage 132 that is mounted in the tray 131 for movement with the carriage 117. Referring to FIG. 4, for example, the containers 105 are suitably clamped or otherwise held in the tray 131 using the cage 132 so they move substantially conjointly with the tray. As illustrated in FIG. 4, the containers 105 are suitably held in the shaker cage 132 which is mounted on the tray 131 in a substantially horizontal orientation. In other words, the containers 105 have longitudinal axes that are substantially horizontal. Also, as illustrated in FIG. 4, the containers are suitably oriented so the cold fingers 107 are also substantially horizontal. The longitudinal axes of the containers 105 and cold fingers 107 are suitably arranged so they are substantially aligned with the direction of the linear reciprocating motion produced by the shaker system 115.

A system as illustrated in FIGS. 2 and 3 can be purchased commercially. For example, a suitable shaker bath system including the components illustrated in FIGS. 2 and 3 can be purchased from VWR of Radnor, Pa. The commercial systems are designed to hold containers in an upright orientation, contrary to what is shown in FIG. 4. Those skilled in the art will be able to devise various ways to modify the commercially available systems (e.g., using different types of clamping systems) so that they can hold and shake containers 105 while they are in a generally horizontal orientation.

Referring to FIG. 5, the containers 105 suitably contain a fluid including a petroleum product, such as oil (e.g., crude oil). Oil from oil wells is commonly produced along with water, which is commonly referred to as brine because the water typically contains sodium chloride and other salts that may affect the chemistry of the production fluids from an oil field. The oil also contains a number of different hydrocarbons including some that are paraffins. The upper portion of FIG. 5 (labelled A) is a schematic diagram showing stratification of the fluid in the containers 105 in a static condition. Notably, the water or brine forms a layer at the bottom of the container and the oil forms a layer that sits above the water or brine.

The system 101 is suitably configured to form an emulsion from the oil and water in the containers 105. For example, the shaking action imparted to the containers 105 by the shaker system 115 suitably disperses the water or brine into small droplets that are suspended in the oil, as illustrated in the bottom of FIG. 5 (labelled B). The oil and water emulsion characteristics may be different depending on the characteristics of the brine, oil, temperature and the agitation parameters. One possibility is that the water can remain mostly as free water with some oil and water droplets mixing into the other phase at the oil-water interface as depicted in FIG. 5 C. Another possibility is that the water can remain largely as free water at the bottom of the container 105 with variously-sized oil and water droplets getting dispersed into the other phase as depicted in FIG. 5 D. Any of the types of emulsion illustrated in FIGS. 5B-5D can be representative of field conditions because the oil-water emulsion characteristics in a production pipeline can vary with age or throughout the production line as the production fluid is exposed to a varied conditions like temperature and shear. Because of the dynamic environment in the container 105, the system 101 may be referred to as a Dynamic Paraffin Deposition Cell.

The system 101 can be used to evaluate wax deposition under a variety of different conditions. The variables that can be changed include the temperature of the bath or other temperature controlled environment, the temperature of the cold body (e.g., cold finger), the chemistry of the petroleum product (including the components of the oil and/or the components of the brine), the presence and/or dosage of one of more paraffin inhibitors and/or paraffin dispersants, the temperature of the fluid at the time the chemicals are injected, the respective phase (oil or brine) in which the chemical is injected, the percentage of brine injected into the oil, the stroke rate of the shaker bath or other agitation parameters, the coolant flow rate, and other variables. This can help make decisions about which paraffin inhibitors and/or paraffin dispersants to use in connection with specific petroleum products.

One embodiment of using the system 101 to conduct a test includes placing one or more of the containers 105 containing a petroleum product in the temperature controlled environment 103 (e.g., in the temperature controlled bath). The petroleum product suitably includes paraffin or one or more other substances that can solidify or otherwise deposit on the cold finger. The petroleum product may be a sample from an oil field and the test may be designed to test the effectiveness of one or more paraffin inhibitors or paraffin dispersants at limiting wax deposition with that specific sample. Alternatively, the oil sample may be a laboratory standard or more be selected or prepared to have specific characteristics and may be mixed with a specified amount of water or brine selected to have specified characteristics in order to test the effectiveness of various paraffin inhibitors and/or paraffin dispersants in a variety of controlled conditions. Accordingly, the method may include adding one or more paraffin inhibitors and/or paraffin dispersants to the fluid in one or more containers 105.

The containers 105 are suitably loaded on the cage 132 which is mounted on the tray 131, for example as illustrated in FIG. 4 so the longitudinal axes of the containers and the cold fingers 107 are substantially parallel to the direction of the linear reciprocating motion produced by the shaker system 115. The temperature of the bath 103 is suitably set to be a relatively warm temperature compared to the temperature of the coolant from the cooling system 109. For example, the temperature of the bath is suitably set to be slightly above or slightly below the wax appearance temperature. The coolant is circulated through the cold finger 107 to cool the cold finger to a temperature that is below a temperature of the bath.

The agitation system 115 (e.g., the shaker system described above) is used to move the container 105 and the cold body 107 to create ongoing relative movement of the fluid in the container relative to the cold body. For example, the shaker system 115 in the illustrated embodiment suitably shakes the container 105 and cold body 107 back and forth in a reciprocating motion while the container is in the bath 103 and while the cooling system 109 circulates coolant the cold finger 107 to create a condition in which wax in the fluid may deposit on the cold finger. In the case in which the fluid contains two different types of fluids (e.g., water or brine and oil) the movement of the container 105 by the agitation system suitably forms or maintains an emulsion in the fluid (e.g., as illustrated schematically in FIGS. 5B-5D). For example, the shaking of the container 105 by the shaker system 115 suitably creates an alternating series of shearing movements of the fluid relative to the cold finger and instances in which at least some of the fluid is stationary relative to the cold finger. For example, the movement of the fluid will tend to lag the movement of the respective container 105 and the cold finger 107 when the container and cold finger are being accelerated by the shaker system 115. During this time, a shearing interaction exists at the interface of the cold finger 107 and the fluid. At some point as the container 105 and cold finger are decelerated by the shaker system 115 near the end of the stroke, the fluid will catch up with the cold finger 107 and for at least a brief moment there will be substantially no relative movement between the fluid and the cold finger 107 at the interface between the fluid and the cold finger. As the shaker system 115 continues to accelerate the container 105 and cold finger 107 in the opposite direction to change the direction of movement, the fluid will again move relative to the cold finger at the interface. Due to the momentum imparted on the oil and brine by the container 105 and cold finger 107 assembly and the bi-directional movement of the shaker, the directional flow of the fluid (oil and brine) and the cold finger 107 and container 105 will alternate between being in the same direction and in opposite directions during the test. This creates good mixing of the oil and brine component inside the container, and the fluid inside the container can experience various directional flows which might not be limited to parallel movement along the cold finger assembly 107 but rather movement in multiple directions at various angles (0-360°) relative to the finger assembly.

After the end of a deposition period during which the shaker system 115 continues to shake the container 105 and the cold finger is cooled by the coolant, the cold finger 107 is removed and the amount of wax that has deposited on the cold finger is measured. For example, the wax is suitably melted and weighed to measure how much wax deposited on the cold finger 107. It is also understood that the thickness or volume of the wax deposit could be measured to evaluate the wax deposition during the test.

The test can be varied in a number of different ways. An example of a standard protocol that may be used for conducting tests using the system will now be described to further illustrate how the systems and methods described above may be used. It is understood that the protocol is not required and also that one or more different protocols could be used if desired.

If the test involves oil received from the field, the oil may be in a container in which paraffin has settled out at the bottom of the container due to the cooling of the oil during transit. If necessary, to homogenize the oil and re-melt the paraffin back into the oil matrix the containers are placed into an oven at a temperature significantly higher than the WAT of the oil for 2 to 6 hours depending on the volume of the oil. The oil is vented at regular intervals during the heating period and mixed well to melt the settled wax. A portion of the conditioned oil is finally poured into a glass container and stored until the time of experiment. This subsampled oil is further conditioned and mixed well for an hour before starting a test.

To start the test, subsampled paraffinic oil is placed in the containers 105, which are capped. The containers 105 are conditioned in an oven at a suitable temperature above the WAT for up to about an hour. Any chemicals, such as a paraffin inhibitor and/or paraffin dispersant, that are to be injected in the oil sample are injected into the oil at the specified dose after the conditioning if testing above WAT condition. The treated oil is mixed well and then placed back in the oven for another half an hour. Water or brine is conditioned at the same temperature as the oil for half an hour. The targeted volume of water or brine is injected into the oil to simulate the specific water cut. The cold fingers 107 and the disks they are mounted on are then inserted into the containers 105, which are sealed with a cap 110. The containers 105 are then placed inside the shaker cage 132 and placed in the bath 103 of the system 101 and mounted on the shaker system 131. The temperature of the bath 103 was equilibrated to the target bath temperature beforehand. The shaker operation is turned on at the target stroke rate and the samples in the containers 105 are equilibrated to the bath temperature for typically about half an hour. The equilibration time can be varied from a few minutes to a few hours depending on the test requirements. Any chemicals, such as a paraffin inhibitor and/or paraffin dispersant, that are to be included in the oil sample are injected into the oil at the specified dose after the conditioning if testing below WAT injection. In the case of below WAT injection the shaker operation is continued for another 15 minutes to thoroughly mix the injected chemical(s) into the fluid sample. The mixing time can be varied depending on the test requirements. The chiller coolant temperature was suitably set beforehand so the coolant is already at the desired temperature. Once the thermal equilibration and/or chemical mixing are complete, the chiller lines are connected to the individual cold fingers 107. Coolant is circulated through the cold fingers 107 to cause paraffin or other materials to deposit on the surface of the cold finger. The paraffin deposition period continues for a specified period of time, which can vary from about 15 minutes to about a week, depending on the deposition rate of the paraffin. At the end of the specified time, the shaker system 115 is stopped and the containers 105 are taken out of the bath. Individual cold fingers 107 are taken out of each container and placed inside pre-weighed bottles. The paraffin deposit formed on each cold finger 107 is melted (e.g., in an oven at a target temperature above the melting point of the wax for about an hour). Once cooled, the cold fingers 107 are taken out, leaving the melted paraffin in the pre-weighed bottles. The bottles with the wax are re-weighed and the initial weight is subtracted to quantify the amount deposited on the cold finger 107. Any trace paraffin remaining in the fingers 107 can be wiped with a pre-weighed paper towel and the total paraffin deposit weight is quantified. In some cases, it may be preferable to wipe the wax off the cold finger using a pre-weighed paper towel without using a pre-weighed bottle. The efficacy of the chemical treatment in any condition of interest is benchmarked against untreated sample control or multiple controls. The % inhibition is calculated using the following formula:

% Inhibition=$(W_{untreated} - W_{treated})/W_{untreated} \times 100$

Example 1—Evaluation of Paraffin-Combating Product in Wet Oil

Figure 6A:
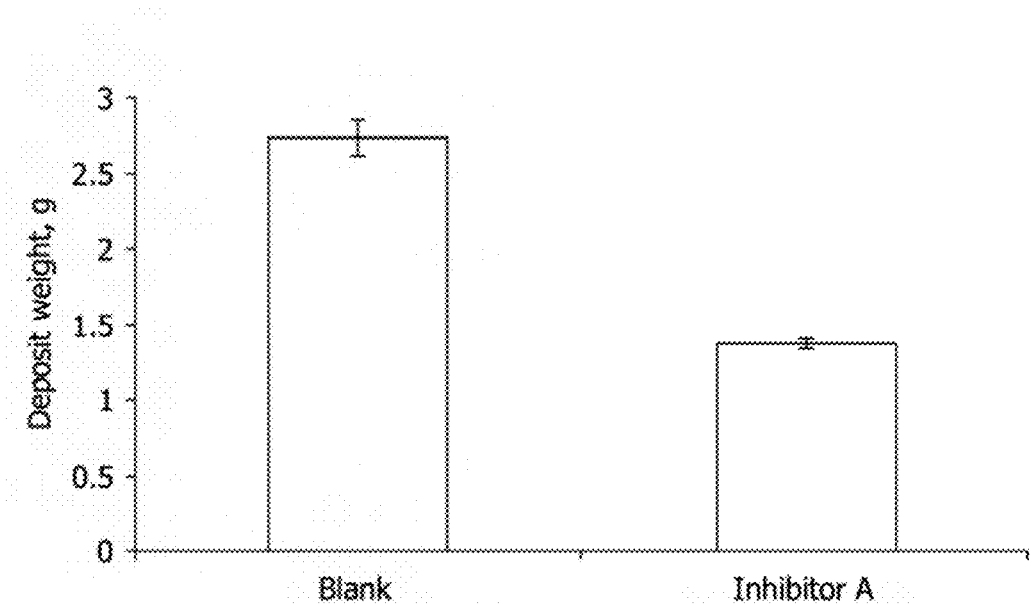
FIG. 6 is a set of graphs A and B showing test results for total deposit and % inhibition in the presence of brine.
Figure 6B:
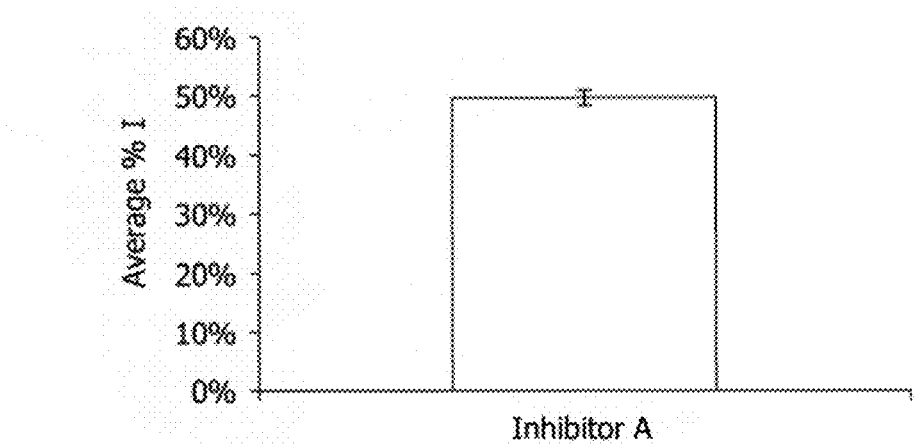

A solution containing 30% by volume non-scaling brine (10000 ppm NaCl and 1000 ppm $CaCl_2$) and a sample of Condensate A (which is a petroleum condensate known to contain paraffin) was tested using the system and methods described above. The wax appearance temperature (WAT) for this condensate was 34 degrees C. The oil was conditioned in 4 different 100 ml commercial Pyrex test bottles from Sigma Aldrich (CLS 1395100) at 60 degrees C. for an hour. The condensate in two of the bottles was treated with a commercially available paraffin-combating product at 500 ppm. The condensate in the other bottles was left untreated by any paraffin inhibitors/paraffin dispersants to serve as controls. The paraffin-combating product was injected into the two bottles, which was followed by mixing and further conditioning in the bottles at 60 degrees C. for half an hour. Then the brine was added to the bottles. Cold finger assemblies (cold finger having about 5/8 inch outer diameter and about 2.5 inch length) were then inserted into each of the bottles which were placed on their sides so the cold fingers were horizontal. All four bottles were placed on the shaker in a bath set at 29 degrees C. and mixed well at 100 strokes per minute at fixed 20 mm stroke length for half an hour. At that point the cold fingers were connected to lines from the chiller and coolant (which was set to 5 degrees C. beforehand) was circulated through the cold fingers while the shaker shook the bottles, and the cold fingers therein, back and forth along the longitudinal axis of the cold fingers to start a wax deposition period. The wax deposition period continued for 18 hours. The wax deposits were melted after the end of the wax deposition period to quantify how much material had been deposited on each of the cold fingers. The results, which are shown graphically in FIG. 6, were that the two untreated control samples had paraffin deposits weighing an average of about 2.7 grams. However, the two samples that had been treated with the paraffin-combating product had paraffin deposits weighing only about 1.4 grams. This shows that the paraffin-combating product was successful at inhibiting the deposition of paraffin. The percentage inhibition (% I) by the paraffin-combating product under these conditions was about 50 percent, as indicated in part B of FIG. 6. This example demonstrates that the testing systems and methods described above can effectively screen paraffin combating products.

Example 2—Evaluation of Paraffin-Combating Products in Dry and Wet Oil

Figure 7A:
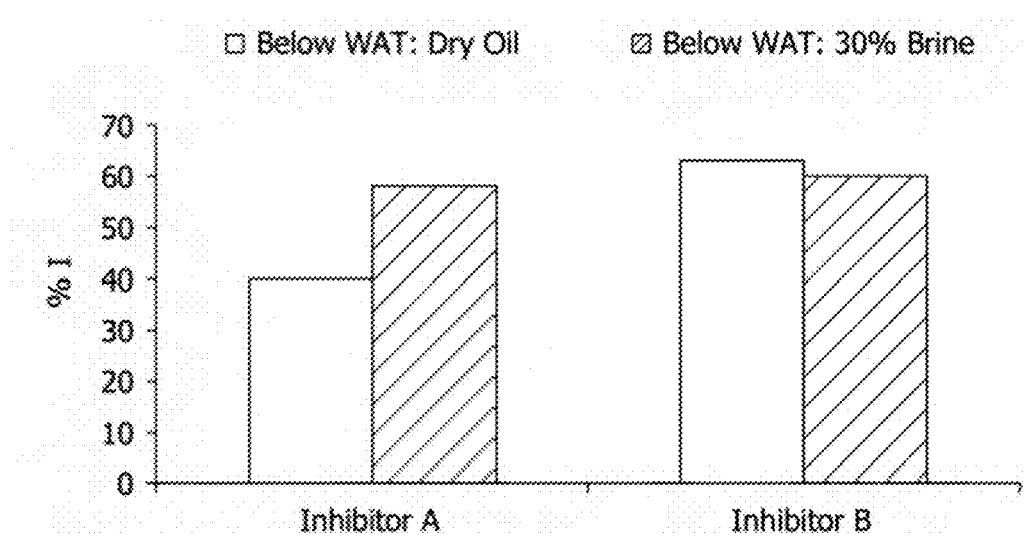
FIG. 7 is a set of graphs A and B showing results of tests evaluating effectiveness of different chemicals in dry oil and brine at two different temperatures.
Figure 7B:
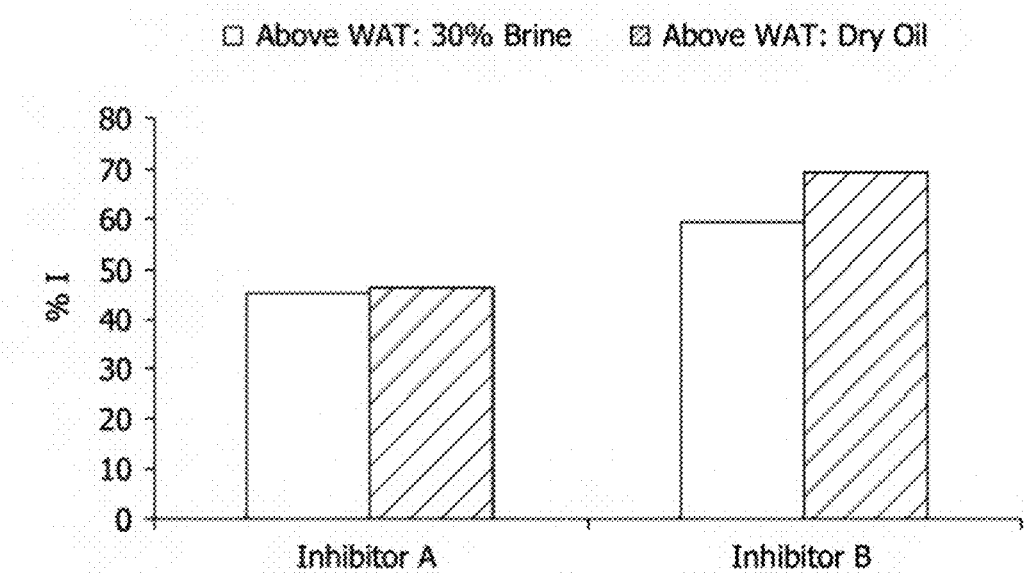

Two different commercially available paraffin-combating products (Product A and Product B) were tested in dry oil and also in wet oil, which contained 30% non-scaling synthetic brine by volume (10000 ppm NaCl and 1000 ppm $CaCl_2$). A sample of Condensate A was used as the oil in both the wet oil and the dry oil tests. The paraffin-combating products were tested at both above and below WAT for Condensate A along with controls. For the above WAT testing, the bath was maintained at 39 degrees C. (5 degrees C. above the WAT). For the below WAT testing, the bath was maintained at 29 degrees C. (5 degrees C. below the WAT). The cold fingers were maintained at 5 degrees C. for all of the tests. Except as noted the testing methods were identical to the methods described above in Example 1. The results are shown in FIG. 7.

The results show that the different paraffin-combating products performed differently in different conditions. For example, in the dry oil tests, the presence of brine had a significant effect on the performance of Product A. The presence of brine also had a noticeable effect on the performance of Product B in the above WAT testing. The tests also showed that Product B performed either better than Product A or about the same as Product A in all of the conditions tested. Consequently, the results illustrate that the testing is an effective way to screen various paraffin-combating products at above and below WAT conditions in presence and absence of brine.

Example 3—Dosage Variation

The effect of dosage variation on various commercially available paraffin-combating products was carried out on Condensate C (WAT 39 degrees C.) in the presence and absence of a 10% synthetic brine. The brine was made by adding the salts listed below in Table 1 to 2 liters of de-ionized water.

TABLE 1

| Salts in synthetic brine | |
|---|---|
| Species | Weight, g |
| NaCl | 34.214 |
| KCl | 0.37 |
| CaCl2 2H2O | 15.34 |
| MgCl2 6H2O | 1.38 |
| SrCl2 6H2O | 1.808 |
| NaHCO3 | 0.606 |
| NaBr | 0.394 |
| Borax | 1.184 |
| NaAc | 0.706 |

Figure 8:
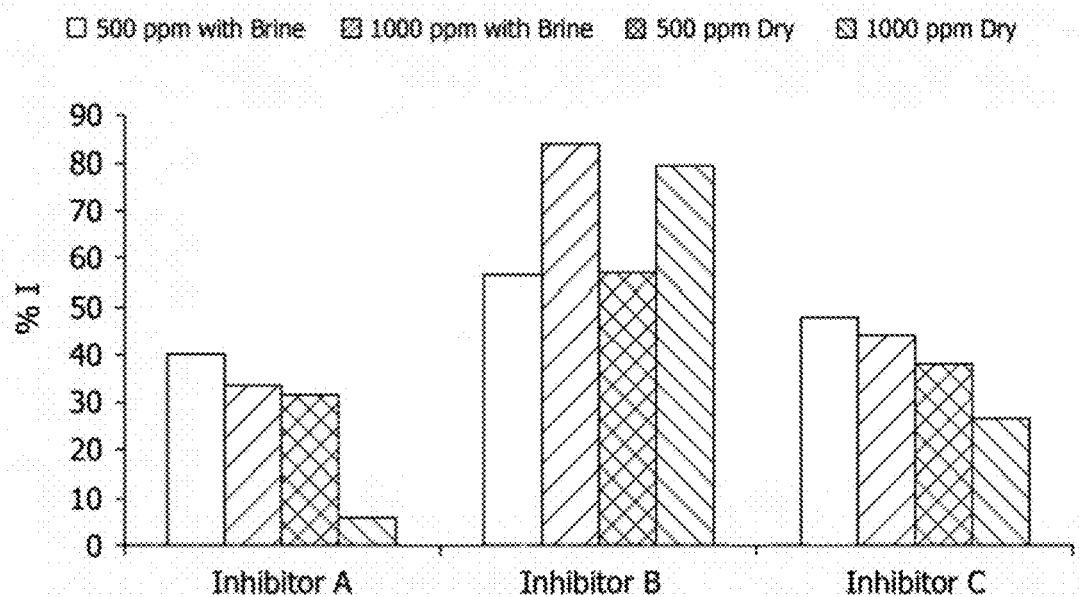
FIG. 8 is a graph showing results of tests evaluating the effectiveness of different chemicals at different dosages in dry oil and brine.

Three different commercial paraffin-combating products, Product A, Product B, and Product C, were tested at 500 ppm and also at 1000 ppm to understand the dosage response for each product. The tests were conducted for each paraffin-combating product in dry oil and also with brine. Untreated controls were also tested. Each test was conducted substantially according to the method described in Example 1 except the synthetic brine was used instead of the non-scaling brine in Example 1 and the paraffin-combating products were different. The results are shown in FIG. 8, which shows the percentage inhibition (% I) for each of the paraffin-combating products under each of the four different conditions. The results indicate that Product A and Product C both performed better at 500 ppm than they did at 1000 ppm. On the other hand, Product B performed better at 1000 ppm. Products A and C also performed better in brine than they did in dry oil. The results also show that Product B outperformed the other paraffin-combating products in all conditions.

Example 4—Evaluation of Paraffin Dispersants in Brine

Three different paraffin dispersants (A, B, and C) at 1000 ppm were tested in two different Condensates: Condensate A (WAT 34 degrees C.) and Condensate B (WAT 42 degrees C.). These paraffin dispersants did not include any paraffin inhibitors. Untreated controls were also tested. The tests were conducted substantially as described in Example 1, except as noted. The oil solution included 10% brine. The brine had the same composition as the synthetic brine in Example 3. The surfaces of the cold fingers were maintained at 5 degrees C. while the temperature of the bath was maintained at 29 degrees C. for Condensate A (i.e., 5 degrees below the WAT for Condensate A) and at 32 degrees C. for Condensate B (i.e., 10 degrees below the WAT for Condensate B).

Figure 9:
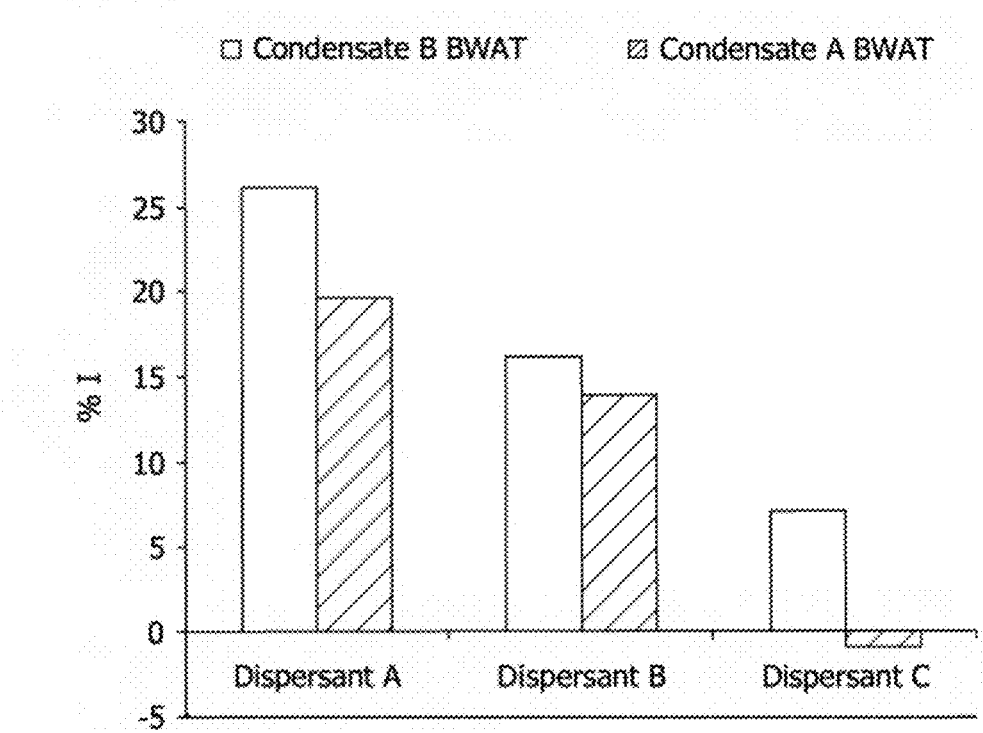
FIG. 9 is a graph showing results of tests evaluating the effectiveness of different chemicals in two different petroleum condensates.

The results are shown in FIG. 9, which shows the % inhibition (% I) for the three paraffin dispersants. A clear ranking for the paraffin dispersants was possible based on this data. In particular, Dispersant A performed better than the other dispersants in both condensates. Dispersant C performed worse than the other dispersants in both condensates.

Further tests were conducted on condensate B for performance differentiation of these dispersants at above WAT condition. The above WAT tests were conducted in substantially the same way as described above except the bath temperature was maintained at 47 degrees C. (i.e., 5 degrees above the WAT). The above WAT data was then compared with the below WAT data from FIG. 9.

Figure 10:
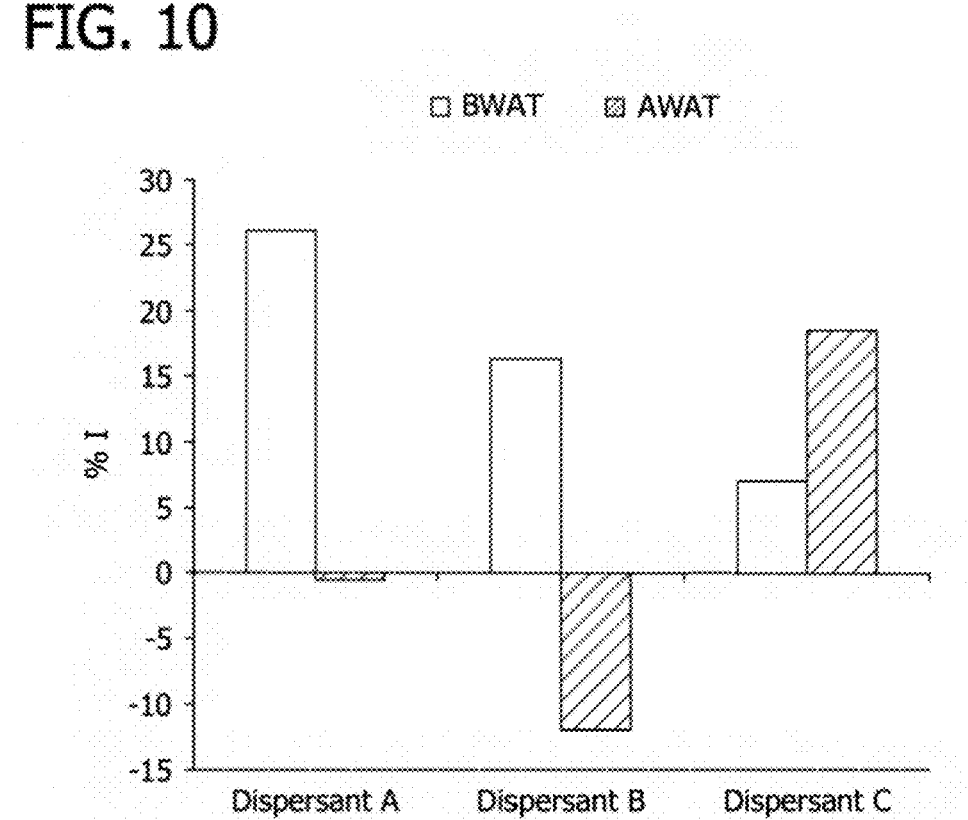
FIG. 10 is a graph a showing results of tests evaluating the effectiveness of three different chemicals at different temperatures.

The results of this comparison are shown in FIG. 10, which shows the % inhibition (% I) of all three dispersants under below WAT (BWAT) and above WAT (AWAT) conditions. The results show all of the paraffin dispersants were less effective at in the above WAT condition. It should also be noted that the ranking of the dispersants were changed as the bulk temperature of the oil changed. Thus, the tests indicate the most effective paraffin dispersant depends on the conditions in which it is used.

Example 5—Evaluation of Water Cut

These tests were conducted to investigate whether or not performance of paraffin dispersants depends on factors related to the water cut in the production line. Three different paraffin dispersants (A, B, and C) were tested at both 10% brine and 20% percent brine in Condensate A. Again, these paraffin dispersants did not include any paraffin inhibitors. The brine was a synthetic brine listed in table 1. Untreated controls were also tested. The tests were conducted with the bath held at a temperature of 29 degrees C. (i.e., 5 degrees below the WAT for Condensate A). Except as noted, the tests were conducted according to the specifications in Example 1.

Figure 11:
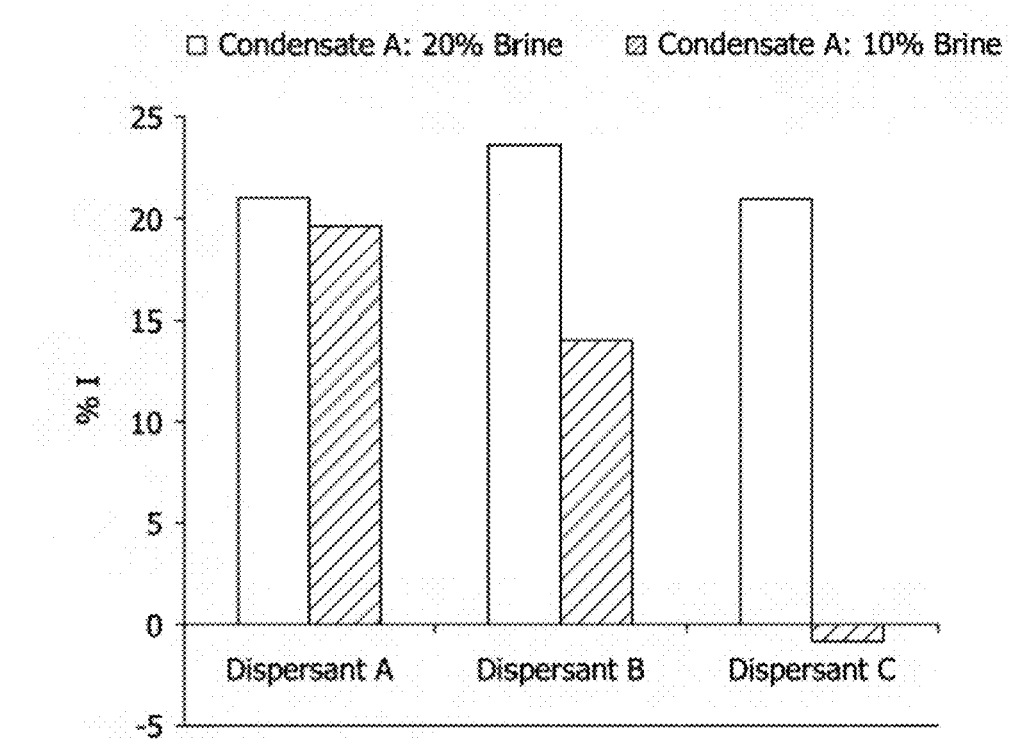
FIG. 11 is a graph showing results of tests evaluating the effectiveness of three different chemicals at two different water cut percentages.

The results are shown in FIG. 11, which shows the percentage inhibition (% I) of each paraffin dispersant in the brine-containing samples. The results show that each of the paraffin dispersants is more effective with the higher brine concentration. This is especially true for dispersants B and C. These results demonstrate that the effectiveness of paraffin dispersants can depend on the amount of brine in the production fluids.

Example 6—Evaluation of Brine Chemistry

Figure 12:
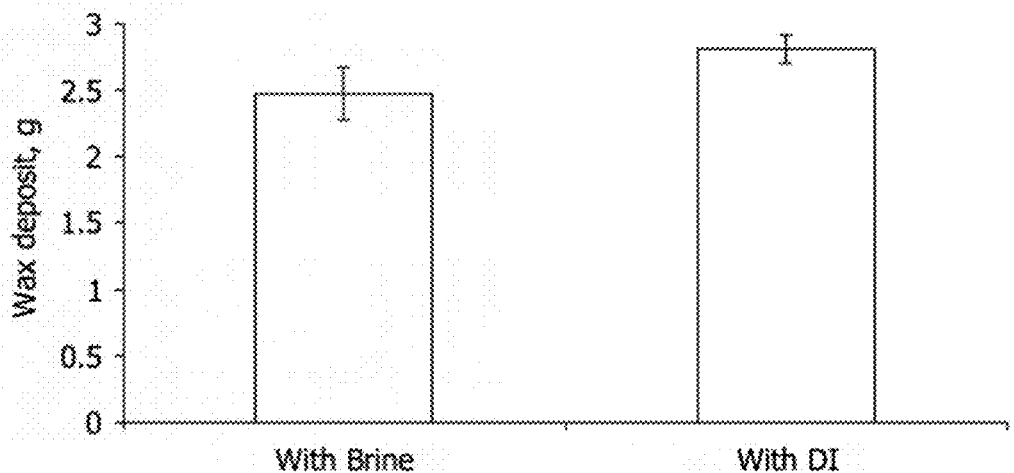
FIG. 12 is a graph showing the results of a test comparing the effectiveness of one chemical with different brine chemistries.

Effect of brine chemistry on paraffin deposition has been investigated on untreated Condensate A in presence of around 27% water cut. In one sample, the water component was a non-scaling brine (10000 ppm NaCl, 1000 ppm $CaCl_2$) in the other sample the water component was de-ionized water. The bath temperature was maintained at 29 degrees C. (i.e., 5 degrees below the WAT) and the cold fingers were maintained at 5 degrees C. The results are show in FIG. 12, which shows the total wax deposits by weight for each sample. The results show that a change in salinity of the brine can slightly affect the amount of paraffin deposition.

Figure 13:
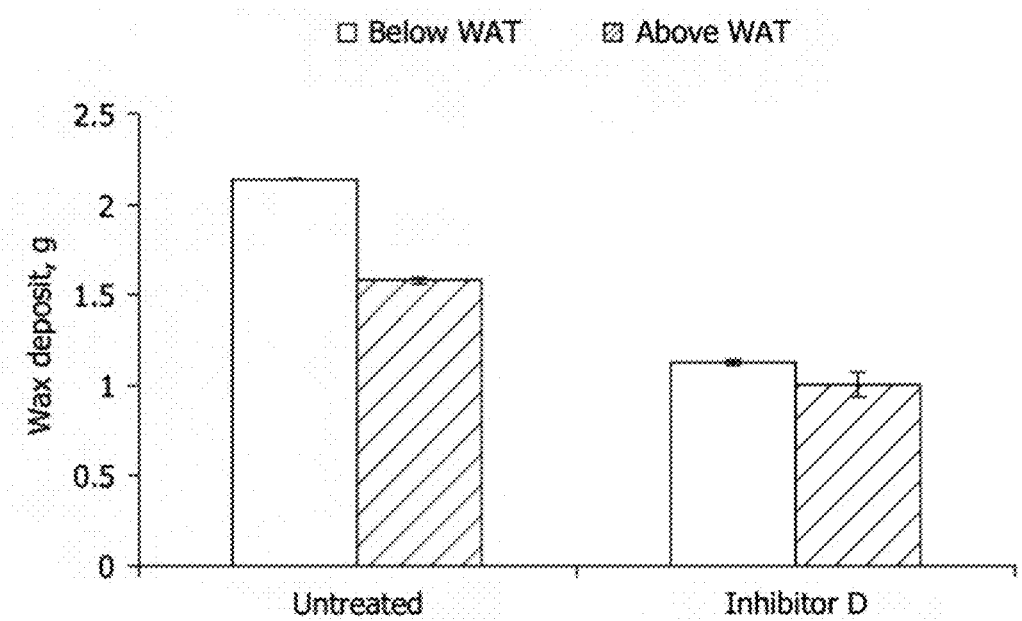
FIG. 13 is a graph showing test results for total deposit for untreated and treated petroleum condensate at different temperatures.

Example 7—Dynamic Paraffin Deposition Cell (DPDC) Test—Reproducibility at Above and Below WAT Conditions A solution containing 16% by volume non-scaling brine and a sample of Condensate 1 (which is a petroleum condensate known to contain paraffin) was tested using the system and methods as described above in Example 1. The brine had the salt composition listed in Table 2 in 2 liter DI water. The wax appearance temperature (WAT) for this condensate was 42 degrees C. The oil was conditioned in eight pyrex test bottles at 60 degrees C. for an hour. The condensate in four of the bottles was treated with an experimental paraffin-combating product Inhibitor D at 500 ppm. The condensate in the other four bottles was left untreated by any paraffin inhibitors/paraffin dispersants to serve as controls. The paraffin-combating product was injected into four of the bottles, which was followed by mixing and further conditioning in the bottles at 60 degrees C. for half an hour. Then the brine was added to the bottles. Cold finger assemblies were then inserted into each of the bottles which were placed on their sides so the cold fingers were horizontal. Two of each of the treated and untreated bottles were placed on the shaker in a bath set at 45 degrees C. (i.e., 3 degrees above the WAT for Condensate 1) and mixed well at 100 strokes per minute at fixed 20 mm stroke length for half an hour. The other half of the treated and untreated bottles were placed on the shaker in a bath set at 37 degrees C. (i.e., 5 degrees below the WAT for Condensate 1) and mixed well at 100 strokes per minute at fixed 20 mm stroke length for half an hour. At that point the cold fingers were connected to lines from the chiller and coolant (which was set to 15 degrees C. beforehand for the above WAT test and 5 degrees C. for the below WAT test) was circulated through the cold fingers while the shaker shook the bottles, and the cold fingers therein, back and forth along the longitudinal axis of the cold fingers to start a wax deposition period. The wax deposition period continued for 6 hours. The wax deposits were melted after the end of the wax deposition period to quantify how much material had been deposited on each of the cold fingers. The results, which are shown graphically in FIG. 13, were that the two untreated control samples at below and above WAT conditions had paraffin deposits weighing an average of about 2.2 and 1.6 grams, respectively. However, the two samples that had been treated with the paraffin-combating product at below and above WAT conditions had paraffin deposits weighing only about 1.2 and 1.0 grams, respectively. This shows that the paraffin-combating product was successful at inhibiting the deposition of paraffin. This example demonstrates that the testing systems and methods described above can effectively screen paraffin combating products with reasonable accuracy.

TABLE 2

Salts in synthetic brine

| Species | Weight, g |
|---|---|
| KCl | 0.236 |
| CaCl2 2H2O | 5.461 |
| SrCl2 6H2O | 0.608 |
| MgCl2 6H2O | 1.422 |
| NaCl | 52.056 |

Example 8—DPDC Vs. Cold Finger Test

Above WAT DPDC Vs. Cold Finger.

The above WAT procedure of Example 7 was repeated for two different paraffin combating products referred to as Inhibitor C and Inhibitor D.

A cold finger test was conducted in a commercial PSL cold finger apparatus. Condensate 1 (1 liter) was conditioned in an oven at 60° C. for an hour. 80 ml of conditioned oil was poured into test beakers. The inhibitor C and D were injected at 500 ppm into the oil for the target treatments. Magnetic stir bars were placed inside the oil samples. The treated oil was placed into the hot bath which was already set to the target temperature of 45° C. The oil was stirred at 467 rpm for half an hour with a lid placed over the beaker. The chillers connected to the cold finger setups were set to the target test temperature of 15° C. The lids were taken out and the cold finger assemblies were lowered into the beakers. The paraffin deposition test was conducted for the target time of 6 h. At the end of the test the cold finger assembly was taken out of the test beakers and the finger slips were detached from the individual cold fingers and the paraffin deposits were quantified by weight of the deposit. The % inhibition values were calculated as described above.

Figure 14:
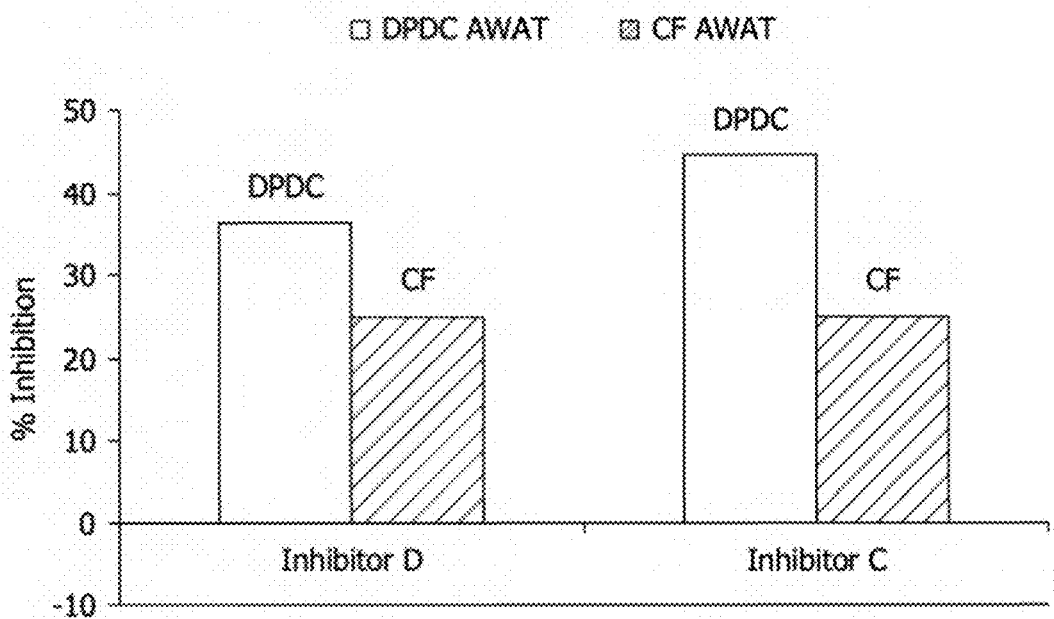
FIG. 14 is a graph showing test results for paraffin inhibition for two different paraffin inhibitors using DPDC above WAT and cold finger test methods.

The comparative results are shown in FIG. 14. The DPDC results including 16% brine showed better performance of products and performance differentiation. The % inhibition of Inhibitor D was about 37% for DPDC and about 24% for cold finger. The % inhibition of Inhibitor C was about 44% for DPDC and about 24% for cold finger.

Figure 15:
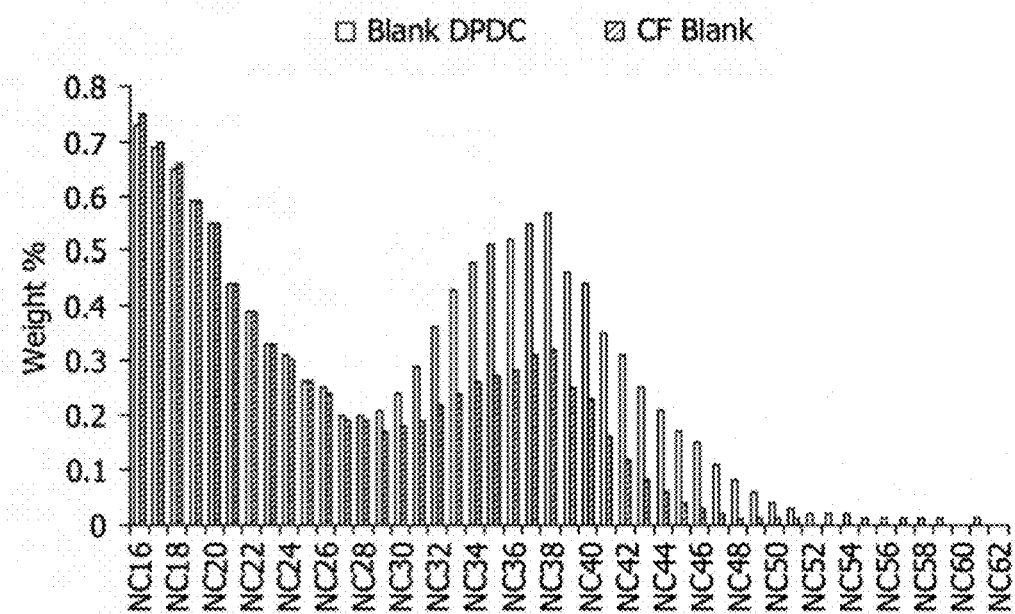
FIG. 15 is a graph showing weight percentage for different paraffin carbon chains (NC refers to normal straight chain carbons) plotted against the carbon numbers using DPDC above WAT and cold finger test methods.

High temperature gas chromatography was conducted in a third party laboratory using the melted deposits from the cold finger and DPDC tests. The % weight data for different paraffin carbon chains (NC refers to normal straight chain carbons) were plotted against the carbon numbers as shown in FIG. 15. The DPDC above WAT deposits show an increase in wax content compared to the conventional cold figure device and procedure.

Figure 16:
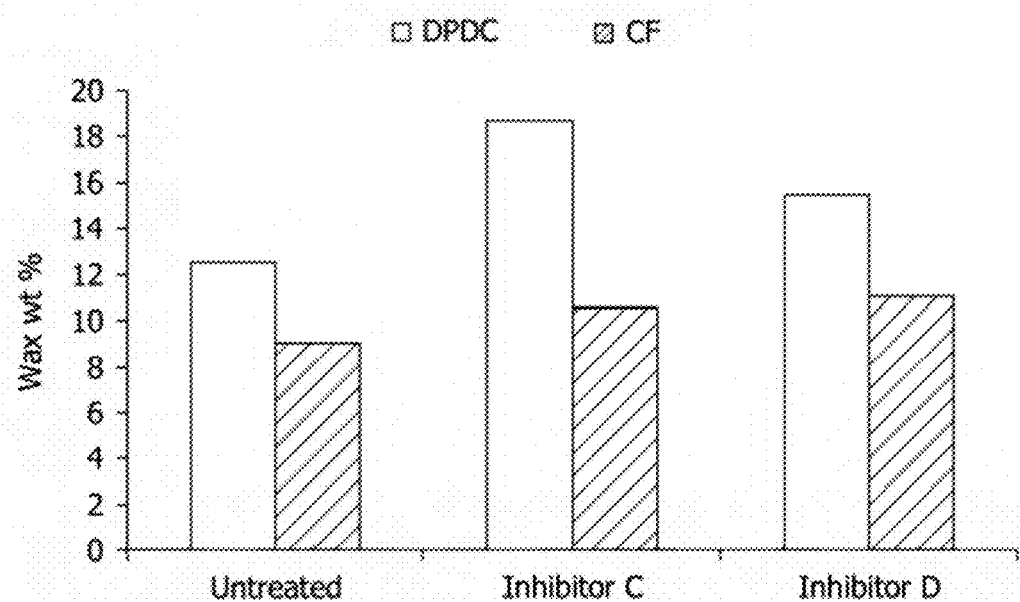
FIG. 16 is a graph showing test results for concentration of wax in the deposit (% weight of wax) for two different paraffin inhibitors and control using DPDC above WAT and cold finger test methods.

The weight % of normal chain carbons were summed from C16 onwards to calculate the total concentration of wax (wt. %) and plotted in FIG. 16. DPDC above WAT deposits showed an increase in wax content as compared to conventional cold finger deposits.

Below WAT DPDC Vs. Cold Finger.

The below WAT procedure of Example 7 was repeated for two different paraffin combating products referred to as Inhibitor C and Inhibitor D.

A cold finger test was conducted in a commercial PSL cold finger apparatus. Condensate 1 (1 liter) was conditioned in an oven at 60° C. for an hour. 80 ml of conditioned oil was poured into test beakers. Magnetic stir bars were placed inside the oil samples. The treated oil was placed into the hot bath which was already set to the target temperature of 37° C. The oil was stirred at 467 rpm for half an hour with a lid placed over the beaker. The inhibitor C and D were injected at 500 ppm into the oil for the target treatments. The treated oil was stirred for another 15 minutes to mix well. The chillers connected to the cold finger setups were set to the target test temperature of 5° C. The lids were taken out and the cold finger assemblies were lowered into the beakers. The paraffin deposition test was conducted for the target time of 6 h. At the end of the test the cold finger assembly was taken out of the test beakers and the finger slips were detached from the individual cold fingers and the paraffin deposits were quantified by weight of the deposit. The % inhibition values were calculated as described above.

Figure 17:
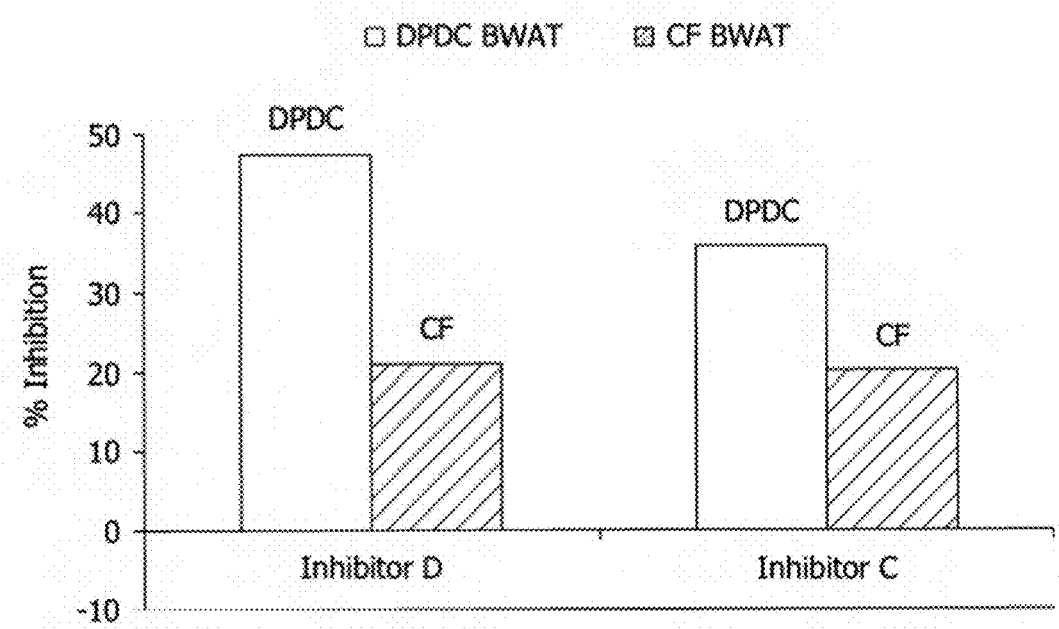
FIG. 17 is a graph showing test results for paraffin inhibition for two different paraffin inhibitors using DPDC below WAT and cold finger test methods.

The comparative results are shown in FIG. 17. The DPDC below WAT results including 16% brine showed better performance of products and performance differentiation. The % inhibition of Inhibitor D was about 47% for DPDC and about 21% for cold finger. The % inhibition of Inhibitor C was about 36% for DPDC and about 20% for cold finger.

Figure 18:
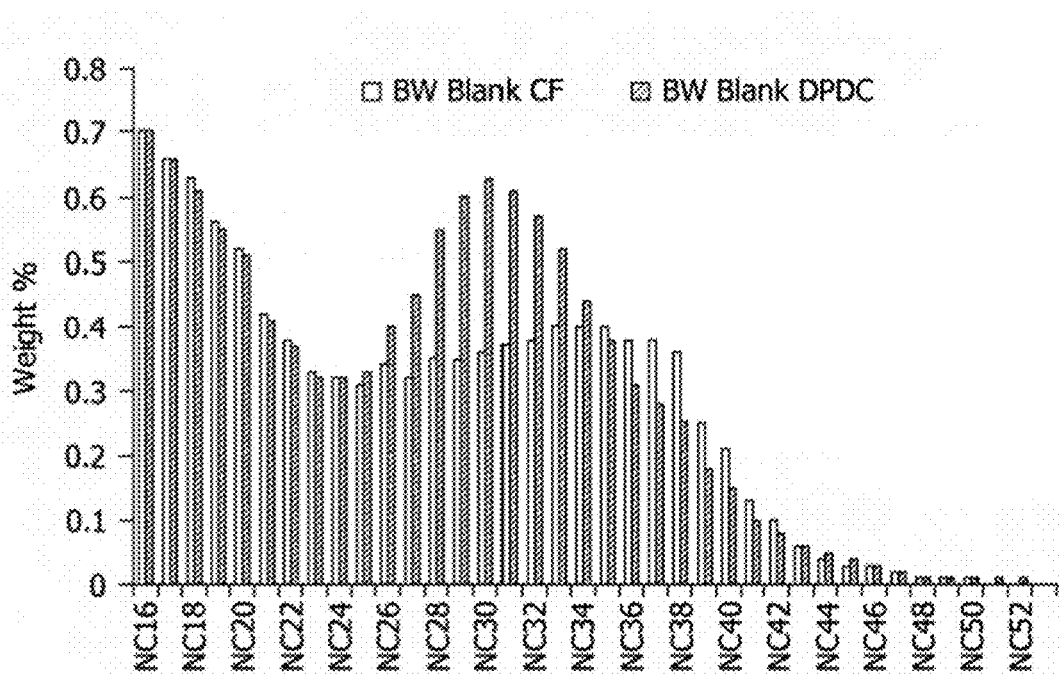
FIG. 18 is a graph showing weight percentage for different paraffin carbon chains (NC refers to normal straight chain carbons) plotted against the carbon numbers using DPDC below WAT and cold finger test methods.

High temperature gas chromatography was conducted in a third party laboratory using the melted deposits from the cold finger and DPDC below WAT tests. The % weight data for different paraffin carbon chains (NC refers to normal straight chain carbons) were plotted against the carbon numbers as shown in FIG. 18. The DPDC below WAT deposits show an increase in wax content compared to the conventional cold figure device and procedure.

Figure 19:
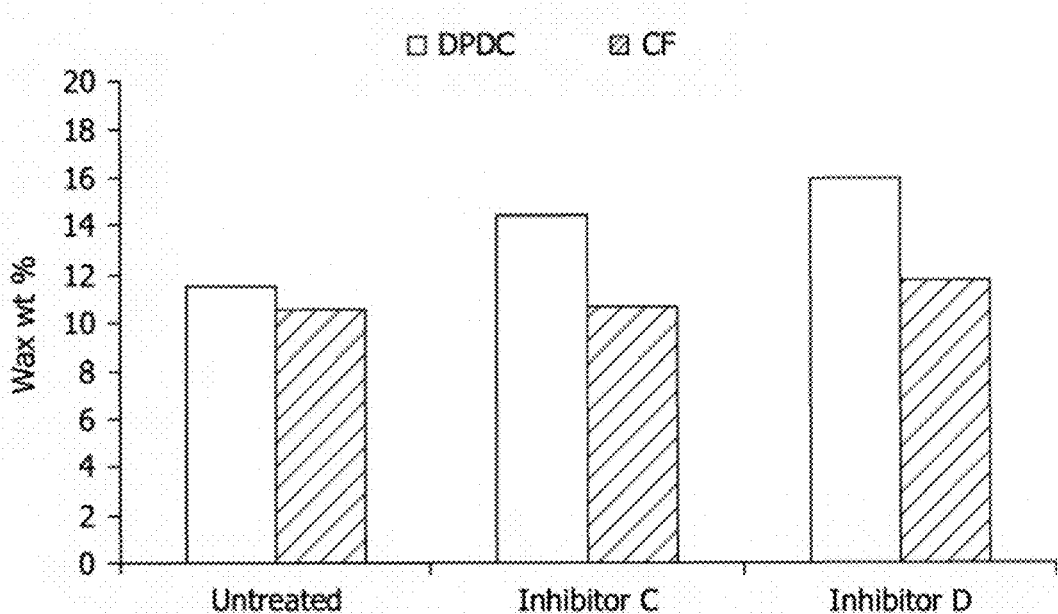
FIG. 19 is a graph showing test results for concentration of wax in the deposit (% weight of wax) for two different paraffin inhibitors and control using DPDC below WAT and cold finger test methods.

The weight % of normal chain carbons were summed from C16 onwards to calculate the total concentration of wax (wt. %) and plotted in FIG. 19. DPDC below WAT deposits showed an increase in wax content as compared to conventional cold finger deposits.

Figure 20:
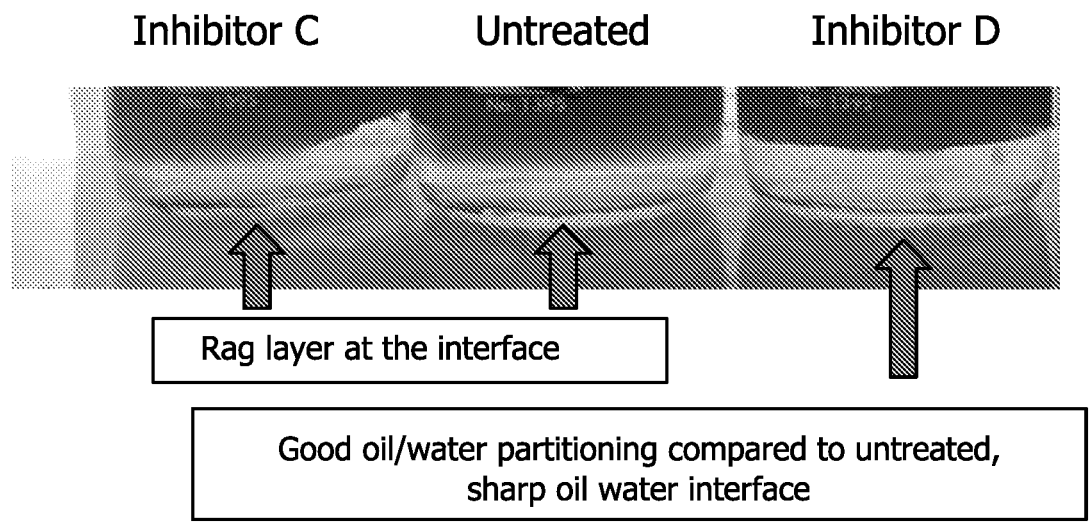
FIG. 20 depicts oil/water partitioning of DPDC below WAT test samples.

At the end of the DPDC below WAT test, water fouling was visually assessed as shown in FIG. 20. The untreated and Inhibitor C samples showed a rag layer at the interface, while the Inhibitor D sample showed good oil/water partitioning and a sharp oil-water interface.

Example 9—Water Cut Effect Study

Figure 21:
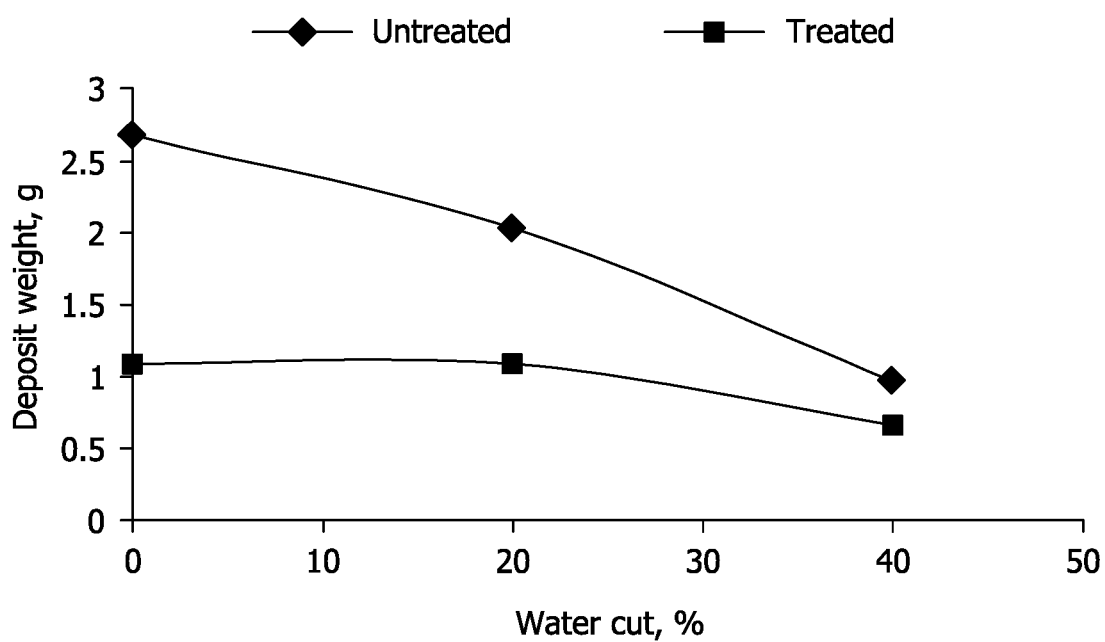
FIG. 21 is a graph showing results of tests evaluating deposit weight for treated and untreated samples at three different water cut percentages.

The DPDC below WAT tests were conducted as described in Example 7 with the following changes. A different light crude oil C was used. The bath temperature was kept at 25° C. The finger temperature was kept at 5° C. Three tests were conducted at 0% water cut (106 ml oil); 20% water cut (78.8 ml oil and 21.2 ml brine) and 40% water cut (63.6 ml oil and 42.4 ml brine). The brine composition as listed in Table 2 was used for conducting this experiment. Inhibitor C was used at 1000 ppm. Tests were conducted for 18 h. The deposit weight for each water cut is reported in FIG. 21. As water cut increased, the amount of paraffin deposited decreased.

Figure 22:
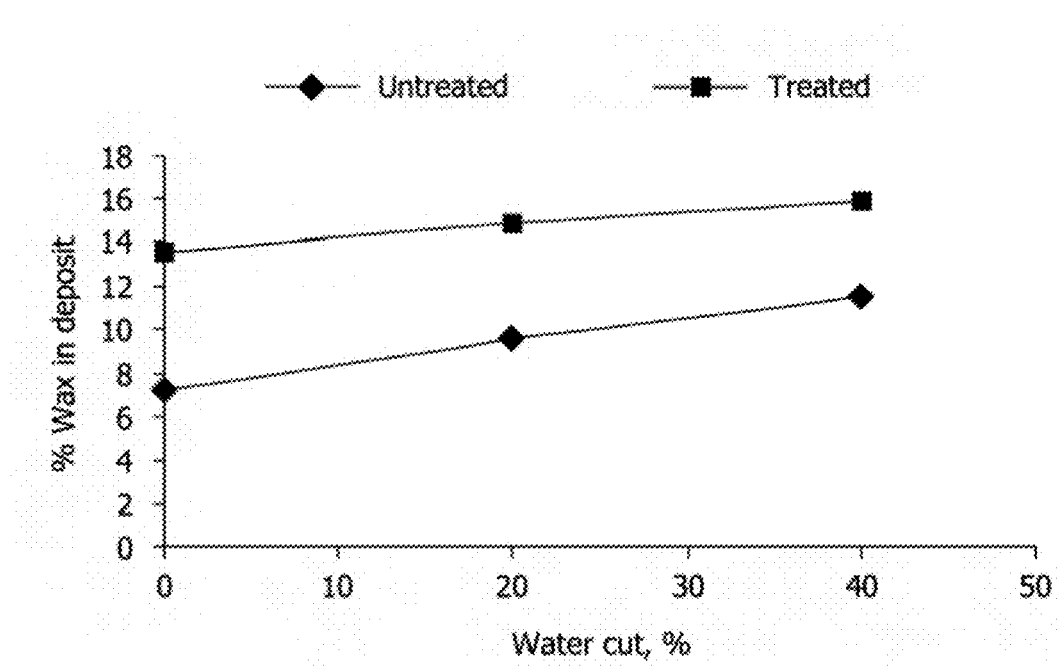
FIG. 22 is a graph showing results of tests evaluating the percentage of wax in the deposits of treated and untreated samples at three different water cut percentages.

The wax deposit samples for the DPDC below WAT test conducted for this study were melted and the wax content was analyzed by TA instrument Q20 model DSC (differential scanning calorimetry) as follows. Around 64 of melted wax was injected into the TA instrument DSC pan. The lid for the pan was placed and the pan was sealed. The prepared pan was placed inside the DSC instrument chamber along with an empty reference pan. The pan was heated to 120° C. in an inert atmosphere of nitrogen. The sample was cooled to 0° C. at 4° C./m in cooling rate. The sensor records the difference in heat flow from the two samples. The DSC curve is a record of this difference versus temperature. The area under the cooling exotherm was integrated and the % wax was calculated considering the average latent heat of melting for wax to be 200 J/g. As shown in FIG. 22, as water cut increased, wax content of the paraffin deposits increased.

Discussion of Examples

Collectively, the examples set forth above demonstrate that the testing systems and methods described herein are effective at providing valuable information concerning the effects of various paraffin-combating chemicals in various conditions. Without being bound by a particularly theory, it is believed the several factors may allow the test systems and methods described herein to more effectively mimic field conditions in the laboratory. For example, the agitation system 115 along with the movement of the container 105 and cold body 107 is quite effective at generating and maintaining an emulsion if water or brine is included in the fluid sample. The agitation system 115 along with the movement of the container 105 and cold body 107 is also very effective at preventing or eliminating unwanted stratification within the sample fluid. Also, conditions at the interface of the cold body 107 and the fluid include periods of relatively high shear following by periods of stagnation or near stagnation over small scale portions of the interface, which may be a better way to mimic the turbulent flow inside a pipeline. Moreover, the conditions at the interface of the cold body 107 and the fluid are fairly uniform over the length of the cold finger, especially compared to some convention cold finger testing systems in which a magnetic mixing bar or other structure is positioned at one location in the container to agitate the fluid sample. This is not intended to be an exhaustive list of factors that contribute to the functionality of the test systems and methods described herein, but is instead provided to highlight some of the differences between the systems and methods described herein and convention cold finger systems and methods.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

What is claimed is:

1. A system for evaluating wax deposition, the system comprising:
   a temperature controlled environment;
   a container for holding a fluid, the container being positioned in the temperature controlled environment;
   a cold body extending into the container;
   a cooling system connected to the cold body and configured to circulate a coolant through the cold body to cool the cold body; and
   an agitation system configured to produce relative movement between the cold body and the fluid in the container by moving the container and the cold body.

2. The system as set forth in claim 1 wherein the cold body is a cold finger.

3. The system as set forth in claim 2 wherein the cold finger has a longitudinal axis and the agitation system is configured to move the container back and forth in a direction that includes a component that is parallel to the longitudinal axis of the cold finger.

4. The system as set forth in claim 3 wherein the agitation system is configured to move the container back and forth in a direction that is substantially parallel to the longitudinal axis of the cold finger.

5. The system as set forth in claim 1 wherein the container and/or the cold body has a longitudinal axis and the container and/or the cold body is oriented so the longitudinal axis of the container extends in a horizontal direction.

6. The system as set forth in claim 5 wherein the longitudinal axis of the container or the cold body is substantially horizontal.

7. The system as set forth in claim 1 in combination with the fluid in the container, the fluid comprising a petroleum product.

8. The system as set forth in claim 7 wherein the fluid comprises a paraffinic crude oil.

9. The system as set forth in claim 1 wherein the agitation system is configured to move the container back and forth in a linear reciprocating motion.

10. The system as set forth in claim 1 wherein the container is one of a plurality of containers and the cold body is one of a plurality of cold bodies, wherein the cooling system is connected to each of the cold bodies and configured to circulate the coolant through each of the cold bodies to cool the cold bodies, the system further comprising a support for holding the plurality of containers in the temperature controlled bath, the agitation system comprising a moving system for moving each of the containers back and forth in a reciprocating motion by moving the support.

11. The system as set forth in claim 1 wherein the temperature controlled environment comprises a temperature controlled bath.

12. A method of evaluating wax deposition, the method comprising:
    placing a container holding a fluid comprising a petroleum product in a temperature controlled environment;
    circulating a coolant through a cold body positioned to extend into the container to cool the cold body to a temperature that is below a temperature of the temperature controlled environment;
    moving the container and the cold body in a manner that creates ongoing movement of the fluid relative to the cold body due to the momentum of the fluid and acceleration of the container and the cold body while coolant is circulated through the cold body to create a condition in which wax in the fluid may deposit on the cold body; and
    measuring the amount of wax that has deposited on the cold body.

13. The method as set forth in claim 12 wherein the wax comprises paraffin.

14. The method as set forth in claim 12 wherein moving the container comprises moving the container in a manner that forms an emulsion from the fluid.

15. The method as set forth in claim 12 wherein the fluid comprises a mixture of oil and brine, a paraffin deposition inhibitor, and/or a paraffin dispersant.

16. The method as set forth in claim 12 wherein the fluid has a wax appearance temperature and the temperature controlled environment has a temperature that is above or below the wax temperature.

17. The method as set forth in claim 12 wherein shaking the container back and forth comprises moving the container back and forth in a linear reciprocating motion or creating an alternating series of shearing movements of the fluid relative to the cold finger and instances in which at least some of the fluid is stationary relative to the cold finger.

18. The method as set forth in claim 12 wherein the cold body is a cold finger.

19. The method as set forth in claim 18 wherein the cold finger has a longitudinal axis oriented to extend in a horizontal direction and wherein the longitudinal axis of the cold finger is substantially horizontal.

20. The method as set forth in claim 12 wherein the temperature controlled environment comprises a temperature controlled bath.

* * * * *